US008961962B2

(12) United States Patent
Schuchman et al.

(10) Patent No.: US 8,961,962 B2
(45) Date of Patent: Feb. 24, 2015

(54) ACID CERAMIDASE AND MAMMALIAN CELL SURVIVAL

(75) Inventors: Edward H. Schuchman, Haworth, NJ (US); Efrat Eliyahu, New York, NY (US); Nataly Shtraizent, New York, NY (US); Xingxuan He, Fresh Meadows, NY (US)

(73) Assignee: Mount Sinai School of Medicine, New York, NY (US)

( * ) Notice: Subject to any disclaimer, the term of this patent is extended or adjusted under 35 U.S.C. 154(b) by 1329 days.

(21) Appl. No.: 11/970,393

(22) Filed: Jan. 7, 2008

(65) Prior Publication Data

US 2008/0199450 A1 Aug. 21, 2008

Related U.S. Application Data

(60) Provisional application No. 60/939,178, filed on May 21, 2007, provisional application No. 60/883,661, filed on Jan. 5, 2007.

(51) Int. Cl.
| | |
|---|---|
| *A61K 38/50* | (2006.01) |
| *A61P 15/00* | (2006.01) |
| *C12Q 1/37* | (2006.01) |
| *C12N 5/075* | (2010.01) |
| *C12N 5/00* | (2006.01) |
| *C12N 5/073* | (2010.01) |
| *C12N 5/0793* | (2010.01) |
| *C12N 9/80* | (2006.01) |
| *G01N 33/50* | (2006.01) |

(52) U.S. Cl.
CPC ............ *C12N 5/0609* (2013.01); *C12N 5/0018* (2013.01); *C12N 5/0604* (2013.01); *C12N 5/0619* (2013.01); *C12N 9/80* (2013.01); *C12Y 305/01023* (2013.01); *G01N 33/5058* (2013.01); *G01N 33/5073* (2013.01); *C12N 2501/48* (2013.01); *C12N 2501/70* (2013.01); *G01N 2333/98* (2013.01)
USPC ............ 424/94.6; 435/18; 435/227; 435/366; 435/368; 435/372; 435/374; 435/383; 435/375

(58) Field of Classification Search
None
See application file for complete search history.

(56) References Cited

U.S. PATENT DOCUMENTS

| | | | |
|---|---|---|---|
| 6,258,581 B1 | 7/2001 | Okino et al. | |
| 6,350,768 B1 * | 2/2002 | Bohme et al. | ................. 514/367 |
| 6,489,117 B2 | 12/2002 | Okino et al. | |
| 6,541,218 B1 | 4/2003 | Schuchman et al. | |
| 6,767,741 B1 * | 7/2004 | Epstein et al. | ................. 435/404 |
| RE38,689 E | 1/2005 | Okino et al. | |
| 6,858,383 B2 | 2/2005 | Sabbadini | |
| 6,881,546 B2 | 4/2005 | Sabbadini | |
| 7,018,628 B1 | 3/2006 | Sarkis et al. | |
| 7,232,670 B2 * | 6/2007 | D'Azzo et al. | ................. 435/183 |
| 2003/0157086 A1 | 8/2003 | Tilly et al. | |
| 2004/0039046 A1 | 2/2004 | Deigner | |
| 2004/0247603 A1 | 12/2004 | Sabbadini | |
| 2006/0154252 A1 | 7/2006 | Marguerie et al. | |

FOREIGN PATENT DOCUMENTS

| | | |
|---|---|---|
| JP | 2002-542195 A | 12/2002 |
| JP | 2003-516122 A | 5/2003 |
| JP | 2004-83465 A | 3/2004 |
| WO | 00/62780 A1 | 10/2000 |
| WO | 01/26678 A1 | 4/2001 |
| WO | 2004/057031 A2 | 7/2004 |
| WO | 2006/113289 A2 | 10/2006 |

OTHER PUBLICATIONS

Eliyahu et al., "Acid Ceramidase Is a Novel Factor Required for Early Embryo Survival," Abstract Presented in Mar. 2007.
Eliyahu et al., "Acid Ceramidase Is a Novel Factor Required for Early Embryo Survival," FASEB J. 21:1403-09 (May 2007).
International Search Report and Written Opinion for International Patent Application No. PCT/US08/50418 (Oct. 8, 2008).
Miranda et al., "Infusion of Recombinant Human Acid Sphingomyelinase into Niemann-Pick Disease Mice Leads to Visceral, but Not Neurological, Correction of the Pathophysiology," FASEB J. 14:1988-95 (2000).
Pandey et al., "Recent Advances in the Immunobiology of Ceramide," Exp. Mol. Pathol. 82:298-309 (2007) (E-pub Oct. 12, 2006).
Thon et al., "The Murine TRAIL Receptor Signals Caspase-independent Cell Death Through Ceramide," Experimental Cell Research 312:3808-21 (2006).
Xu et al., "Golgi Alkaline Ceramidase Regulates Cell Proliferation and Survival by Controlling Levels of Sphingosine and S1P," The FASEB Journal 20:1813-25 (2006).
Jan et al., "Sindbis Virus Entry into Cells Triggers Apoptosis by Activating Sphingomyelinase, Leading to the Release of Ceramide," J. Virol. 74(14):6425-32 (2000).
Chavez et al., "Acid Ceramidase Overexpression Prevents the Inhibitory Effects of Saturated Fatty Acids on Insulin Signaling," J. Biol. Chem. 280(20):20148-53 (2005).
Monick et al., "Cooperative Prosurvival Activity by ERK and Akt in Human Alveolar Macrophages Is Dependent on High Levels of Acid Ceramidase Activity," J. Immunol. 173:123-35 (2004).
Auclair et al., "Intra-Articular Enzyme Administration for Joint Disease in Feline Mucopolysaccharidosis VI: Enzyme Dose and Interval," Pediatr. Res. 59(4):538-43 (2006).
Bielicki et al., "Recombinant Canine alpha-L-Fucosidase: Expression, Purification, and Characterization," Mol. Gen. Metabolism 69:24-32 (2000).
Daly & Sands, "Gene Therapy for Lysosomal Storage Diseases," Expert Opin. Invest. Drugs 7(10):1673-82 (1998).

(Continued)

*Primary Examiner* — Lisa J Hobbs
(74) *Attorney, Agent, or Firm* — LeClairRyan, a Professional Corporation

(57) ABSTRACT

The present invention relates to methods of promoting the survival of cells by treating the cells with acid ceramidase. A kit for promoting ex vivo cell survival is also disclosed, as is a method of predicting in vitro fertilization outcome of a female subject.

7 Claims, 14 Drawing Sheets

(56) References Cited

OTHER PUBLICATIONS

Eliyahu et al., "Acid Ceramidase Improves the Quality of Oocytes and Embryos and the Outcome of in Vitro Fertilization," FASEB J. 24:1229-38 (2010).

Eng et al., "Safety and Efficacy of Recombinant Human alpha-Galactosidase a Replacement Therapy in Fabry's Disease," N. Eng. J. Med. 345(1):9-16 (2001).

European Patent Application No. 08727393.4, Supplementary European Search Report (Sep. 9, 2010).

Gao et al., "Delivery of a Retroviral Vector Expressing Human beta-Glucuronidase to the Liver and Spleen Decreases Lysosomal Storage in Mucopolysaccharidosis VII Mice," Mol. Ther. 2(2):233-44 (2000).

Grabowski et al., "Enzyme Therapy in Type 1 Gaucher Disease: Comparative Efficacy of Mannose-Terminated Glucocerebrosidase from Natural and Recombinant Sources," Ann. Intern. Med. 122:33-39 (1995).

Harmatz et al., "Enzyme Replacement Therapy in Mucopolysaccharidosis VI (Maroteaux-Lamy Syndrome)," J. Pediatr. 144:574-80 (2004).

He et al., "Purification and Characterization of Recombinant, Human Acid Ceramidase. Catalytic Reactions and Interactions With Acid Sphingomyelinase," J. Biol. Chem. 278(35):32978-86 (2003).

Huang et al., "A Comparison of the Signal Pathways Between the TNFalpha- and Oridonin-Induced Murine L929 Fibrosarcoma Cell Death," Acta Med. Okayama 59(6):261-70 (2005).

Ioannou et al., "Fabry Disease: Preclinical Studies Demonstrate the Effectiveness of alpha-Galactosidase A Replacement in Enzyme-Deficient Mice," Am J. Hum. Genet. 68:14-25 (2001).

Kakkis et al., "Long-Term and High-Dose Trials of Enzyme Replacement Therapy in the Canine Model of Mucopolysaccharidosis I," Biochem. Mol. Med. 58:156-67 (1996).

Kishida et al., "Docosahexaenoic Acid Enrichment Can Reduce L929 Cell Necrosis Induced by Tumor Necrosis Factor," Biochim. Biophys. Acta 1761:454-62 (2006).

Li et al., "Insertional Mutagenesis of the Mouse Acid Ceramidase Gene Leads to Early Embryonic Lethality in Homozygotes and Progressive Lipid Storage Disease in Heterozygotes," Genomics 79(2):218-24 (2002).

Miranda et al., "Hematopoietic Stem Cell Gene Therapy Leads to Marked Visceral Organ Improvements and a Delayed Onset of Neurological Abnormalities in the Acid Sphingomyelinase Deficient Mouse Model of Niemann—Pick Disease," Gene Ther. 7:1768-76 (2000).

Morita et al., "Oocyte Apoptosis Is Suppressed by Disruption of the Acid Sphingomyelinase Gene or by Sphingosine-1-Phosphate Therapy," Nat. Med. 6(10):1109-14 (2000).

Okino et al., "The Reverse Activity of Human Acid Ceramidase," J. Biol. Chem. 278(32):29948-53 (2003).

Park & Schuchman, "Acid Ceramidase and Human Disease," Biochim. Biophys. Acta 1758:2133-38 (2006).

Rienzi et al., "Predictive Value of Oocyte Morphology in Human IVF: A Systematic Review of the Literature," Hum. Reprod. Update 17(1):33-45 (2011).

Ségui et al., "Stress-Induced Apoptosis Is not Mediated by Endolysosomal Ceramide," FASEB J. 14:36-47 (2000).

Strelow et al., "Overexpression of Acid Ceramidase Protects from Tumor Necrosis Factor-Induced Cell Death," J. Exp. Med. 192(5):601-11 (2000).

Weinreb et al., "Effectiveness of Enzyme Replacement Therapy in 1028 Patients with Type 1 Gaucher Disease After 2 to 5 Years of Treatment: A Report from the Gaucher Registry," Am. J. Med. 113:112-19 (2002).

Witsenburg et al., "Cumulative Live Birth Rates in Cohorts of Patients Treated With in Vitro Fertilization or Intracytoplasmic Sperm Injection," Fertil. Steril. 84(1):99-107 (2005).

International Preliminary Report on Patentability for corresponding International Application No. PCT/US2008/050418 (Jul. 16, 2009).

\* cited by examiner

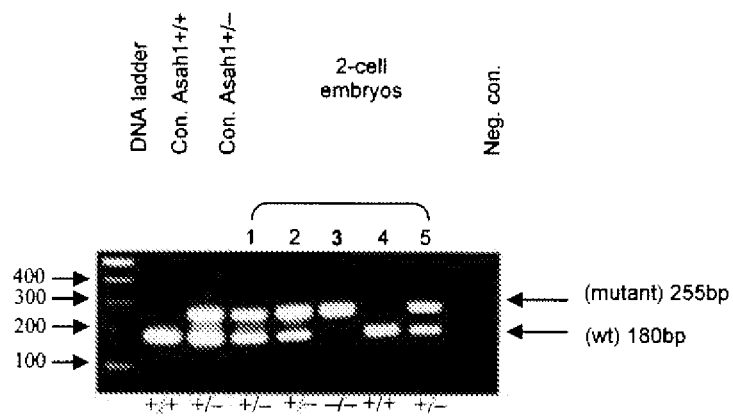
Figure 1
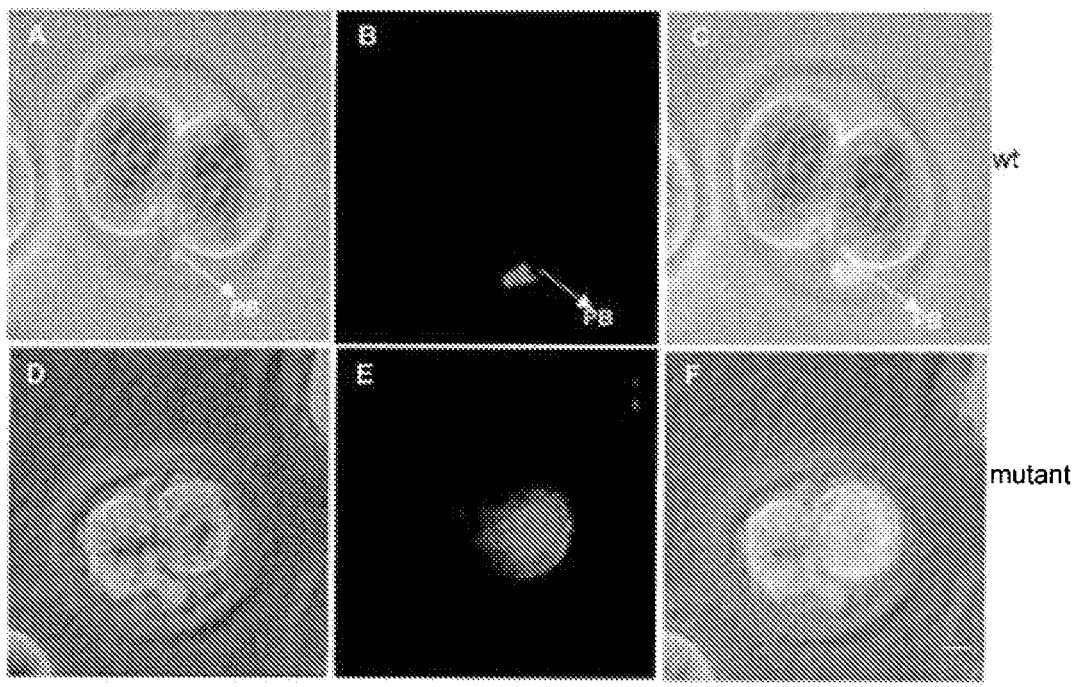
Figures 2A–F

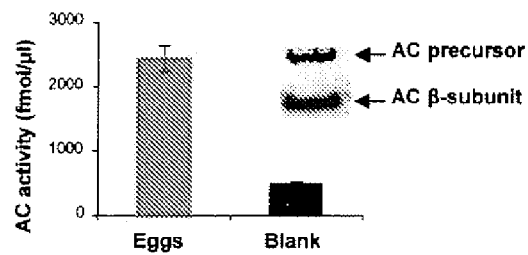
Figure 3
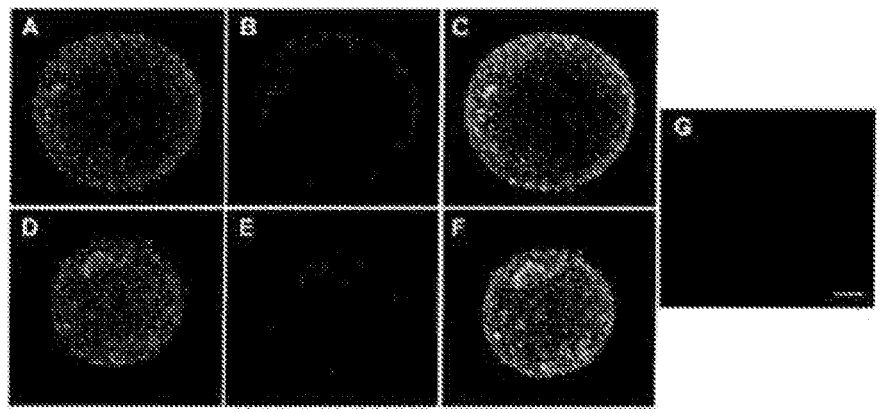
Figures 4A–G
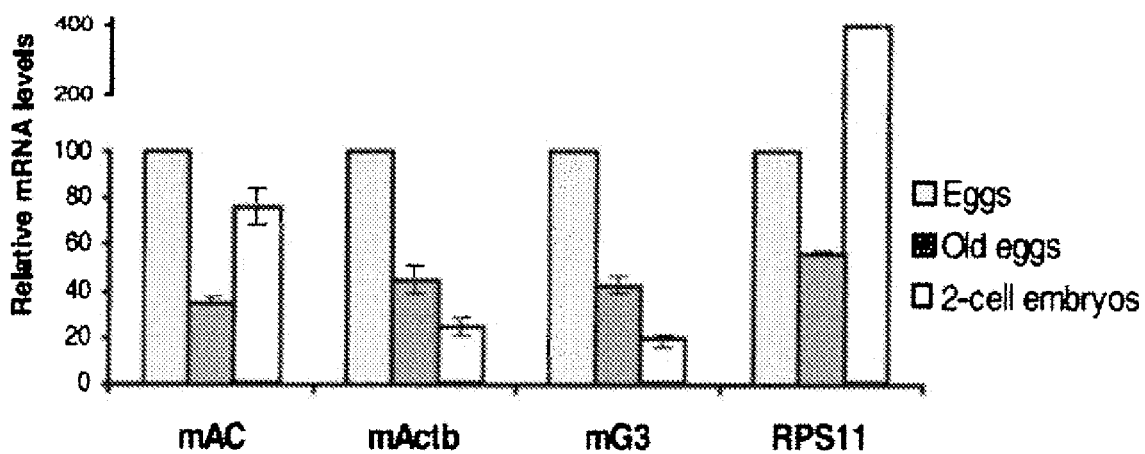
Figure 5

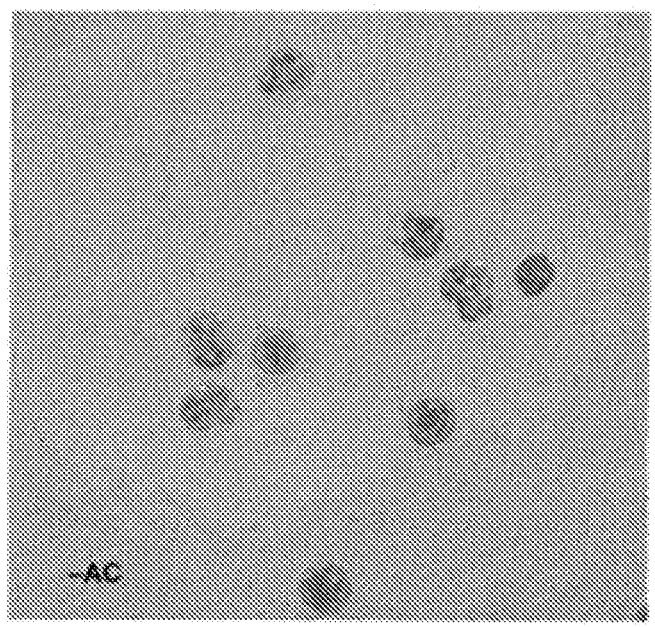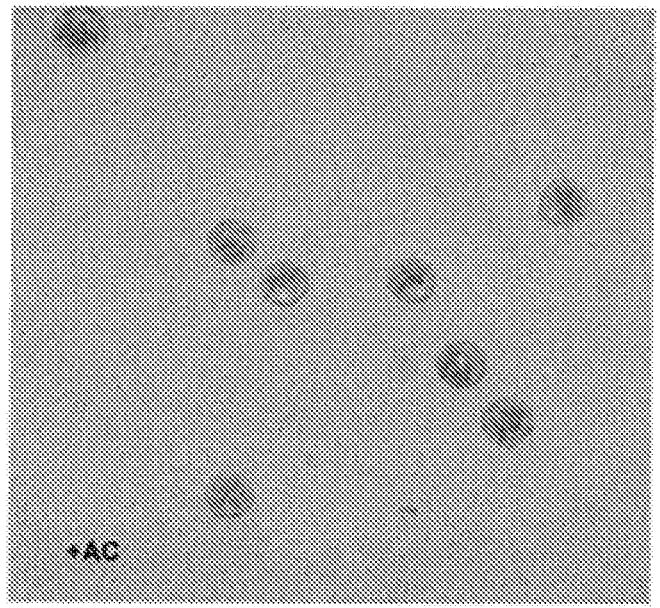
Figures 6A–B

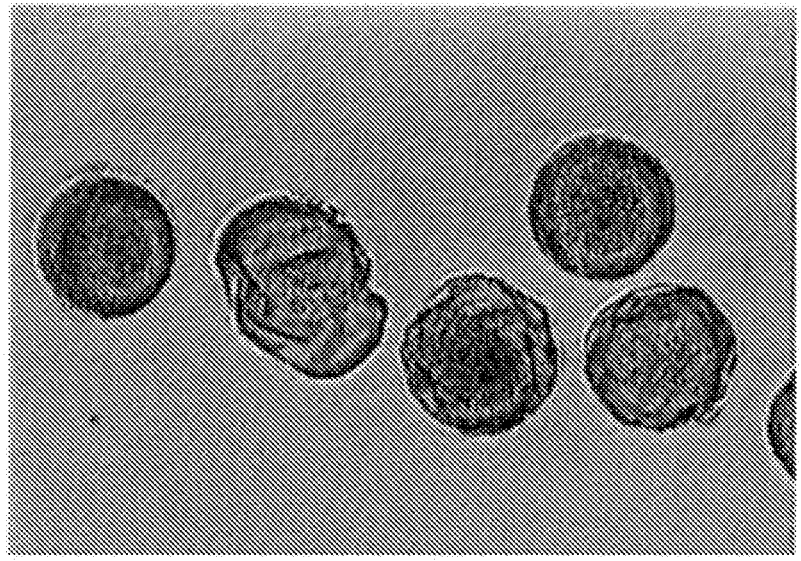
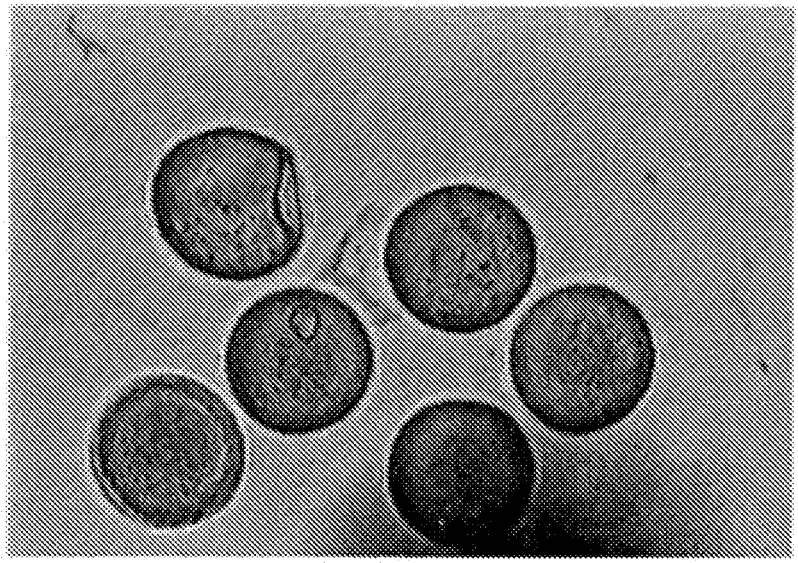
Figures 13A–B

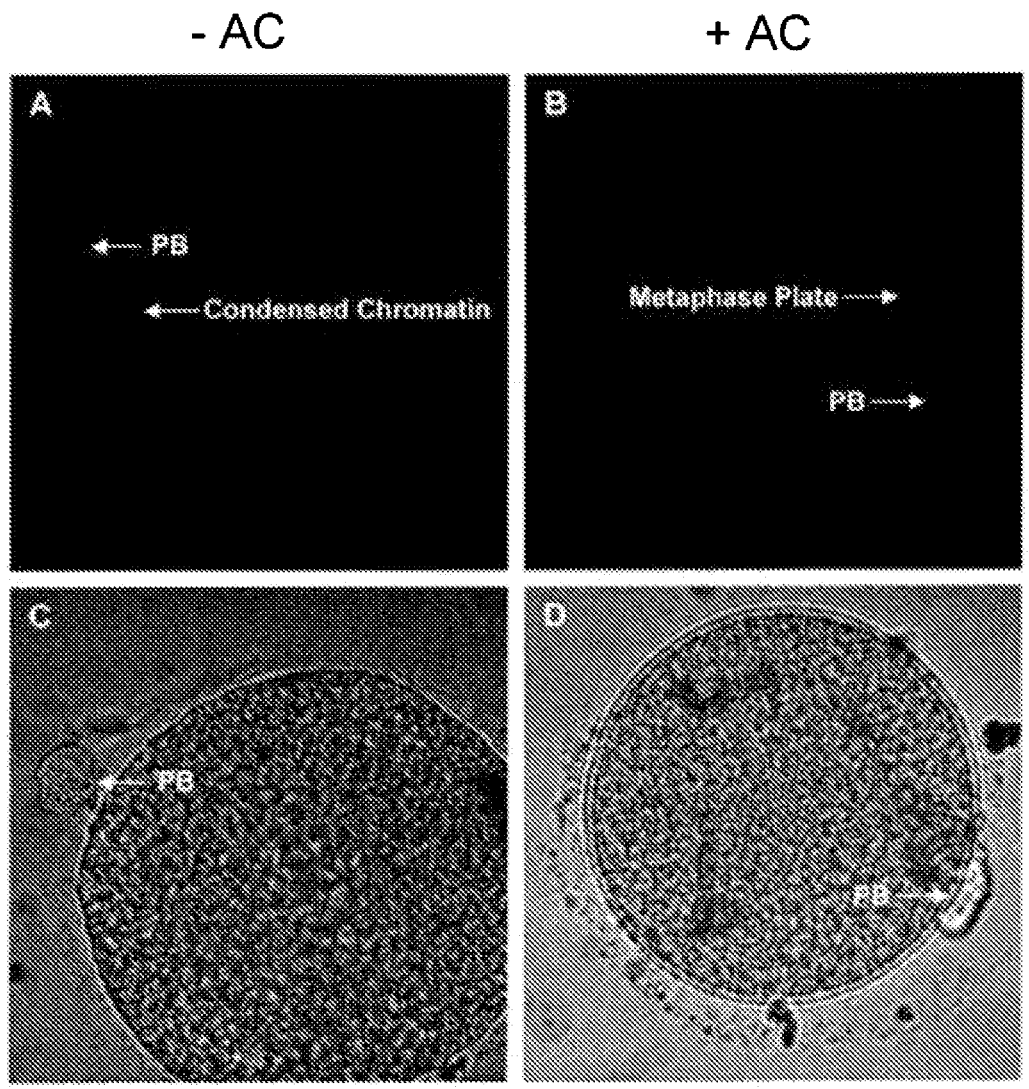
Figures 14A–D

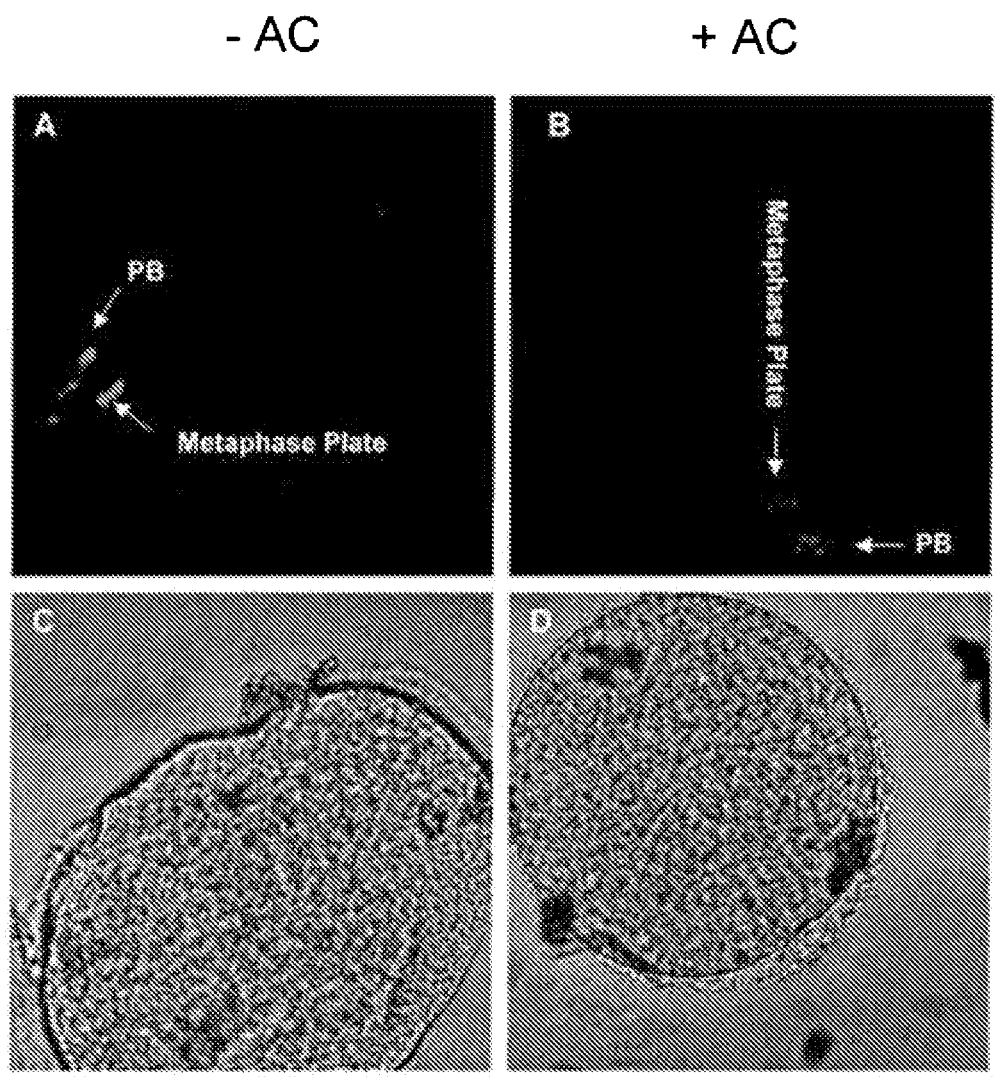
Figures 15A–D

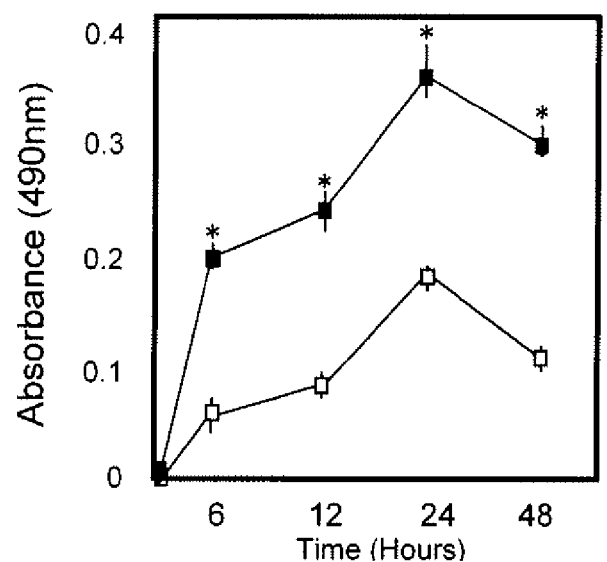
Figure 18
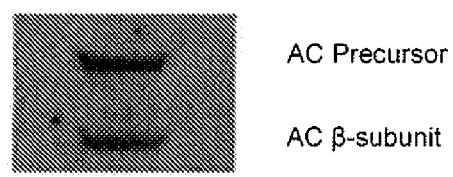
Figure 19
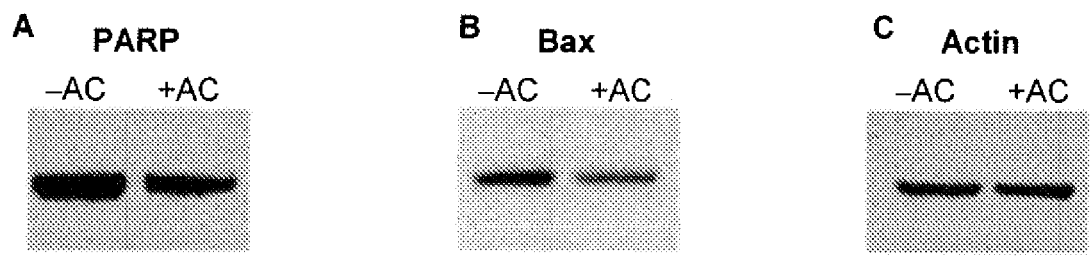
Figures 20A–C

ACID CERAMIDASE AND MAMMALIAN CELL SURVIVAL

This application claims the benefit of U.S. Provisional Patent Application Ser. No. 60/883,661, filed Jan. 5, 2007, and U.S. Provisional Patent Application Ser. No. 60/939,178, filed May 21, 2007, each of which is hereby incorporated by reference in its entirety.

This invention was made with government support under grant number R01 DK54830 awarded by The National Institutes of Health. The government has certain rights in this invention.

FIELD OF THE INVENTION

The present invention relates to methods of promoting cell survival using acid ceramidase.

BACKGROUND OF THE INVENTION

Due to its involvement in the human genetic disorder Farber Lipogranulomatosis ("FD"), acid ceramidase ("AC;" N-acylsphingosine deacylase, I.U.B.M.B. Enzyme No. EC 3.5.1.23) is the most extensively studied member of the ceramidase enzyme family. The protein has been purified from several sources, and the human and mouse cDNAs and genes have been obtained (Bernardo et al., "Purification, Characterization, and Biosynthesis of Human Acid Ceramidase," *J. Biol. Chem.* 270:11098-102 (1995); Koch et al., "Molecular Cloning and Characterization of a Full-length Complementary DNA Encoding Human Acid Ceramidase. Identification of the First Molecular Lesion Causing Farber Disease," *J. Biol. Chem.* 2711:33110-5 (1996); Li et al., "Cloning and Characterization of the Full-length cDNA and Genomic Sequences Encoding Murine Acid Ceramidase," *Genomics* 50:267-74 (1998); Li et al., "The Human Acid Ceramidase Gene (ASAH): Chromosomal Location, Mutation Analysis, and Expression," *Genomics* 62:223-31 (1999)). Growing interest in the biology of this and other ceramidases stems from the fact that these enzymes play a central role in ceramide metabolism. Ceramide is a signaling lipid that is produced in response to various stimuli (Hannun, "Function of Ceramide in Coordinating Cellular Responses to Stress," *Science* 274:1855-9 (1996); Spiegel et al., "Signal Transduction Through Lipid Second Messengers," *Curr. Opin. Cell. Biol.* 8:159-67 (1996)). Normally present in low amounts, in response to these factors, ceramide is rapidly produced at the cell surface, leading to membrane re-organization and downstream signaling that results in apoptosis. After stimulation, AC and/or other ceramidases may then hydrolyze ceramide into the individual fatty acid and sphingosine components (Gatt, "Enzymic Hydrolysis and Synthesis of Ceramide," *J. Biol. Chem.* 238:3131-3 (1963); Gatt, "Enzymatic Hydrolysis of Sphingolipids. 1. Hydrolysis and Synthesis of Ceramides by an Enzyme from Rat Brain," *J. Biol. Chem.* 241:3724-31 (1966); Hassler & Bell, "Ceramidase: Enzymology and Metabolic Roles," *Adv. Lip. Res.* 26:49-57 (1993)). Because ceramide degradation is the only source of intracellular sphingosine (Rother et al., "Biosynthesis of Sphingolipids: Dihydroceramide and Not Sphinganine Is Desaturated by Cultured Cells," *Biochem. Biophys. Res. Commun.* 189:14-20 (1992)), these enzymes may also be rate-limiting steps in determining the intracellular levels of this compound. Importantly, a derivative of sphingosine, sphingosine-1-phosphate ("S1P"), can counteract the apoptotic effects of ceramide (Cuvillier et al., "Suppression of Ceramide-mediated Programmed Cell Death by Sphingosine-1-phosphate," *Nature* 381:800-3 (1996)), leading to the suggestion that ceramidases can be "rheostats" that maintain a proper balance between cell growth and death (Spiegel & Merrill, "Sphingolipids Metabolism and Cell Growth Regulation," *FASEB J.* 10:1388-97 (1996)).

Ovulated eggs undergo molecular changes characteristic of apoptosis unless successful fertilization occurs (Marston & Chang, "The Fertilizable Life of Ova and Their Morphology Following Delayed Insemination in Mature and Immature Mice," *J. Exp. Zool.* 155:237-52 (1964); Tarin et al., "Long-term Effects of Postovulatory Aging of Mouse Eggs on Offspring: A Two-generational Study," *Biol. Reprod.* 61:1347-55 (1999)). While multiple factors, including ceramide, have been characterized as pro-apoptotic elements involved in this process (Perez et al., "A Central Role for Ceramide in the Age-related Acceleration of Apoptosis in the Female Germline," *FASEB J.* 19:860-2 (2005); Miao et al., "Cumulus Cells Accelerate Aging of Mouse Oocytes," *Biol. Reprod.* 73:1025-1031 (2005); Kerr et al., "Morphological Criteria for Identifying Apoptosis," in 1 CELL BIOLOGY: A LABORATORY HANDBOOK 319-29 (Julio E. Celis ed., 1994); Gordo et al., "Intracellular Calcium Oscillations Signal Apoptosis Rather Than Activation in in Vitro Aged Mouse Eggs," *Bio. Reprod.* 66:1828-37 (2002)), little is known about factors that sustain egg or embryo survival.

The present invention is directed to overcoming these and other deficiencies in the art.

SUMMARY OF THE INVENTION

A first aspect of the present invention relates to a method of promoting the ex vivo survival of cells. This method involves providing one or more cells ex vivo and treating the one or more cells with acid ceramidase under conditions effective to promote survival of the one or more cells.

A second aspect of the present invention relates to a method of promoting in vivo survival of one or more cells in a female mammalian subject. This method involves administering to the female mammalian subject acid ceramidase under conditions effective to promote survival of one or more cells in the female mammalian subject.

A third aspect of the present invention relates to a kit for promoting ex vivo primary cell survival. The kit includes a cell culture medium and an acid ceramidase.

A fourth aspect of the present invention relates to a method of predicting in vitro fertilization outcome. This method involves providing a sample of serum or follicular fluid from a female subject and screening the sample for acid ceramidase activity level. The acid ceramidase activity level obtained through said screening is then correlated to a prediction of the outcome of in vitro fertilization for the female subject.

The present invention demonstrates that AC is one factor required for early embryo survival. Gene targeting has been used to inactivate the AC gene (Asah1) in mice (Li et al., "Insertional Mutagenesis of the Mouse Acid Ceramidase Gene Leads to Early Embryonic Lethality in Homozygotes and Progressive Lipid Storage Disease in Heterozygotes," *Genomics* 79:218-24 (2002)). Initial characterization of these animals revealed that heterozygous mice ("Asah1+/−") had a progressive lipid storage disease phenotype, and that a complete loss of AC activity led to the absence of mutant individuals. It remained unclear, however, whether the Asah1−/− embryos were not formed, or, alternatively, if they were formed, whether they died during early embryogenesis.

The present invention describes the use of a combination of molecular, biochemical, and morphological methods to follow the development of individual embryos obtained from Asah1+/− intercrosses. These analyses showed that Asah1−/− embryos could be formed, but underwent apoptotic death at the 2-cell stage. Importantly, these embryos could be rescued by adding S1P to the culture media, permitting their survival to at least the 4-8-cell stage. It was also demonstrated that Asah1 is one of the earliest genes expressed in newly formed embryos. Further, AC is shown to be a predominant protein in unfertilized eggs, and expression of this protein and gene is decreased during egg aging unless fertilization occurs. Overall, these results demonstrate that AC is an essential component of newly formed embryos, and is required for their survival beyond the 2-cell stage.

The present invention also demonstrates that acid ceramidase increases the survival rate of cells in culture. The use of acid ceramidase has several advantages over other potential anti-apoptotic factors: low toxicity, easy delivery, and its unique and specific function.

Being a natural component of normal cells, acid ceramidase should have little or no toxic effects. In addition, providing cells with the precursor (inactive) form would allow the cell itself to control the rate of activation and the amount of the active protein required for survival. Furthermore, controlling ceramide metabolism and producing sphingosine/sphingosine-1-phosphate are the only known functions of acid ceramidase. Thus, increasing acid ceramidase activity in a cell should not affect other cellular signaling pathways.

Acid ceramidase has a natural ability to enter cells through mannose receptors and/or mannose-6-phosphate receptors located on various cell types, including oocytes, neurons, and synovial fibroblasts. Additionally, cells that do not have these receptors contain "scavenging" receptors that can lead to internalization of AC. This implies that administering acid ceramidase into a culture medium can increase the level of the enzyme inside cells in the culture, leading to a reduction in ceramide levels within the cell. It also appears that acid ceramidase can cross the zona pellucida of oocytes, something most molecules cannot do.

Increasing ceramide levels in cells almost always leads to cell death, and ceramidases are the only enzymes that can hydrolyze ceramide. Expression of acid ceramidase in cells has at least two consequences: removal of ceramide, and the production of sphingosine and sphingosine-1-phosphate (two well-characterized, anti-apoptotic lipids). Therefore, without being bound by theory, it is expected that acid ceramidase promotes cell survival in at least two ways: by removing ceramide and by producing sphingosine and sphingosine-1-phosphate. Acid ceramidase is the only known molecule that does both of these.

BRIEF DESCRIPTION OF THE DRAWINGS

FIG. 1 is an agarose gel. Long and nested amplification of the wild-type Asah1 allele ("wt") produced ~9 kb and 180 bp DNA fragments, respectively. Amplification of the disrupted Asah1−/− allele ("mutant") produced ~7 kb and 255 bp DNA fragments, respectively. Genotype analysis was performed on individual 2-cell embryos obtained from Asah1+/− intercrosses using this method, and a representative gel of the nested PCR amplification is shown. Asah1−/− embryos are shown to exist at this stage (lane 3). The negative control ("Neg. con.") did not have template DNA added to the reaction mixture. Lanes "Con. Asah1+/+" and "Con. Asah1+/−" contain template DNA from adult mice known to have the indicated genotype. The size of individual marker fragments in a DNA ladder are indicated on the left side of the panel.

FIGS. 2A-F are light micrographs (FIGS. 2A and 2D), Annexin V-stained images (FIGS. 2B and 2E), and merged images (FIGS. 2C and 2F), showing that Asah1−/− embryos undergo apoptotic death during the 2-cell stage. These figures show the cellular morphology (FIGS. 2A, 2C-D, and 2F) and Annexin V staining pattern (FIGS. 2B-C and 2E-F) of representative wild-type ("wt") and Asah1−/− ("mutant") 2-cell mouse embryos obtained from Asah1+/− intercrosses (see Example 9). "PB" indicates polar bodies. Bar=10 μm.

FIG. 3 is a graph of AC activity and a representative western blot (inset) of cell extracts from unfertilized mouse eggs. Cell extracts from 400 pooled eggs were analyzed by western blot (see Example 10). A goat anti-human AC IgG was used to detect the murine AC precursor protein (55 kDa) and AC β-subunit (40 kDa). For AC activity assays, cell extracts were prepared from 65 pooled eggs, incubated for 22 hours at 37° C. with BODIPY-conjugated C12-ceramide, and then analyzed by HPLC. The AC activity in these extracts was significantly higher in comparison to the blank control (t-test, $p<0.005$). These data show that AC is expressed at high levels in unfertilized, healthy mouse eggs. The data represent mean±S.E.M; n=3 independent experiments.

FIGS. 4A-G are representative immunohistochemistry images of fixed, unfertilized eggs. Goat IgG was used against human AC (FIGS. 4A and 4D), and rat IgG was used against the lysosomal marker Lamp1 (FIGS. 4B and 4E). FIGS. 4C and 4F show merged images. Localization of the primary antibodies was visualized using a fluorescent secondary antibody (Cy-3/2) and laser-scanning confocal microscopy (see Example 5). Eggs labeled only with secondary antibodies were used as a control (FIG. 4G). Bar=10 μm. The data represent three independent experiments, and confirm that AC is expressed at high levels in healthy mouse eggs.

FIG. 5 is a graph of the relative mRNA levels in young unfertilized eggs ("Eggs"), old unfertilized MII eggs ("Old eggs"), and 2-cell embryos, of mice. "mAC": AC mRNA; "mActb": actin beta mRNA; "mG3": glyceraldehyde-3-phosphate dehydrogenase mRNA, "RPS11": ribosomal protein S11 mRNA. The data represent mean±S.E.M.; n=3 independent experiments. These results demonstrate that AC expression decreases in unfertilized mouse eggs as they age. However, if fertilization occurs, AC increases in healthy 2-cell embryos.

FIGS. 6A-B are stained images of mouse oocytes incubated in the absence ("−AC") (FIG. 6A) or presence ("+AC") (FIG. 6B) of acid ceramidase. Bar=10 mm.

FIGS. 8A-P are stained images of denuded and fixed human oocytes at the germinal vesicle stage ("GV"), germinal vesicle breakdown stage ("GVBD"), MI stage, or MII stage. The oocytes were incubated with polyclonal anti-AC antibody (red; FIGS. 8C, 8G, 8K, and 8O), polyclonal anti-LAMP antibody (green; FIGS. 8B, 8F, 8J, and 8N), or the Hoechst DNA-specific fluorochrome 33342 (blue; FIGS. 8A, 8E, 8I, and 8M). FIGS. 8D, 8H, 8L, and 8P show the preceding three images superimposed upon each other ("Merge"), to identify the co-localization of AC with LAMP and/or the cellular DNA. Bar=10 μm. These data are the first to demonstrate expression of AC in human oocytes.

FIG. 9A), anti-acid sphingomyelinase antibody ("ASM") (green; FIG. 9B), or polyclonal anti-AC antibody (red; FIG. 9C). FIG. 9D shows FIGS. 9A-C superimposed upon each other ("Merge"), to identify the co-localization of AC with DNA and/or ASM. Localization of the primary antibodies was imaged using secondary antibodies Cy-3 or Cy-2 and Laser-scanning confocal microscopy. Embryos were graded according to the morphology of the inner and outer cell masses. The data represent three independent experiments. These data are the first to demonstrate expression of AC in human embryos.

FIG. 10A), anti-ASM antibody (green; FIG. 10B), or polyclonal anti-AC antibody (red; FIG. 10C). FIG. 10D shows FIGS. 10A-C superimposed upon each other ("Merge"), to identify the co-localization of AC with DNA and/or ASM. Localization of the primary antibodies was imaged using secondary antibodies Cy-3 or Cy-2 and Laser-scanning confocal microscopy. Embryos were graded according to the morphology of the inner and outer cell masses. The data represent three independent experiments.

FIGS. 13A-B are slides of immature human oocytes cultured in vitro with (FIG. 13B) or without (FIG. 13A) AC.

FIGS. 14A-D are stained images (FIGS. 14A-B) and slides (FIGS. 14C-D) of human oocytes cultured with ("+AC") or without ("−AC") AC. Oocyte DNA was stained with the Hoechst DNA-specific fluorochrome 33342, and the fluorescent signal visualized by Laser-scanning confocal microscopy. Condensed chromatin ("Condensed"), the metaphase plate, and polar bodies ("PB") are indicated. The data represent two independent experiments.

FIGS. 15A-D are TUNEL-stained images (FIGS. 15A-B) and slides (FIGS. 15C-D) of human oocytes cultured with ("+AC") or without ("−AC") AC. The metaphase plate and polar bodies ("PB") are indicated. The data represent two independent experiments.

FIG. 18 is a graph of cell proliferation in primary cat synovial fibroblasts cultured with (closed circles) or without (open circles) human AC, as determined using the MTS reagent (quantified by the absorbance at 490 nanometers). *p<0.001.

FIG. 19 is a western blot of mouse embryonic stem cells, showing the presence of the AC precursor protein (55 kDa) and the AC β-subunit (40 kDa). This shows that AC is expressed at high levels in undifferentiated mouse ES cells.

FIGS. 20A-C are western blots of mouse embryonic stem cells, showing the relative amount of poly(ADP-ribose) polymerase ("PARP") (FIG. 20A), Bax (FIG. 20B), and actin (FIG. 20C) (control) in cells incubated with ("+AC") or without ("−AC") AC. These data demonstrate that when mouse ES cells are grown in the presence of AC, the expression levels of several apoptotic markers (PARP and Bax) are reduced. Proteins were detected using polyclonal antibodies against the respective proteins.

DETAILED DESCRIPTION OF THE INVENTION

Figure 7:
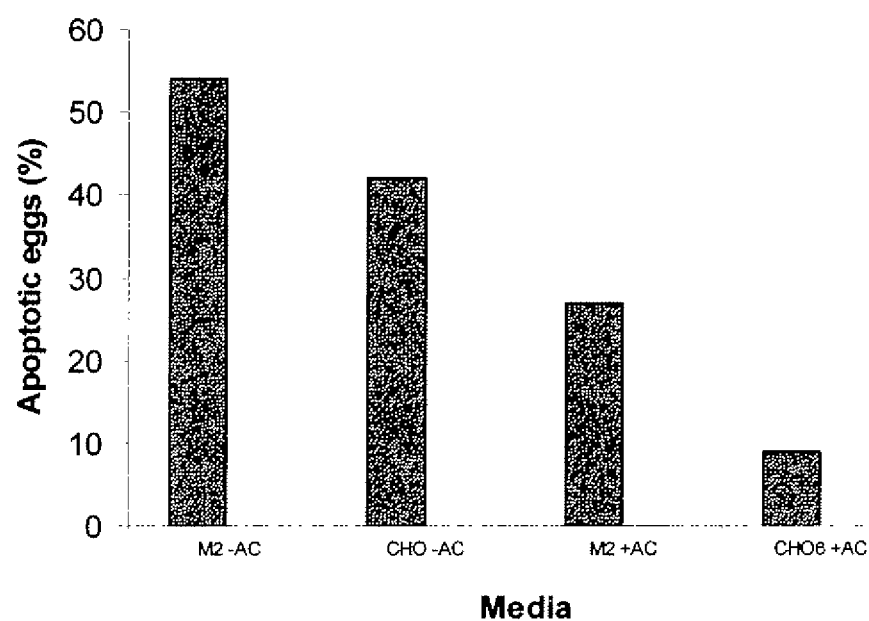
FIG. 7 is a graph illustrating the rate of apoptosis of oocytes incubated in: M2 media without AC ("M2−AC"), media collected from a parental CHO cell line that does not express AC ("CHO−AC"), M2 media supplemented with pure AC (10 ug/ml) ("M2+AC"), or media collected from a CHO cell line that stably expresses and secretes AC ("CHO6+AC"). Data represent three independent experiments.
Figure 8:
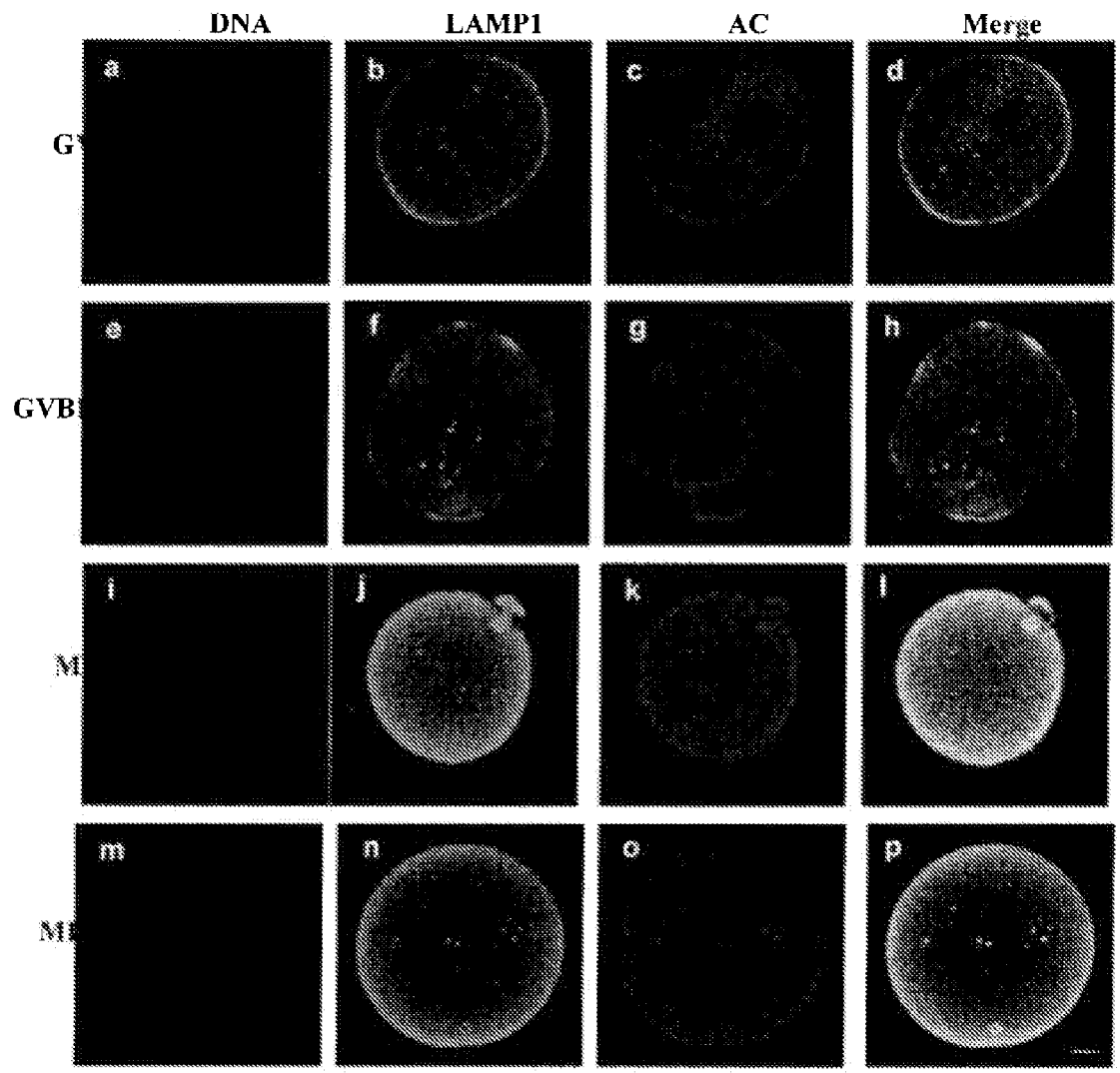
Figure 9:
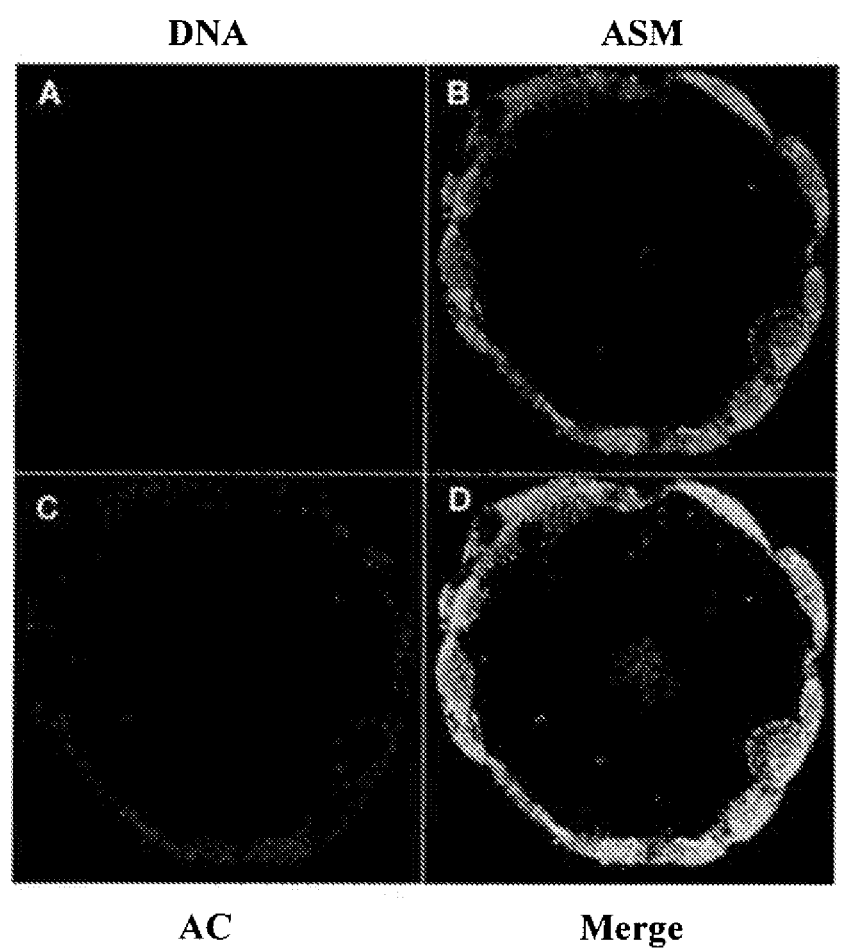
FIGS. 9A-D are stained images of denuded and fixed low grade human embryos. The embryos were incubated with the Hoechst DNA-specific fluorochrome 33342 (blue.
Figure 10:
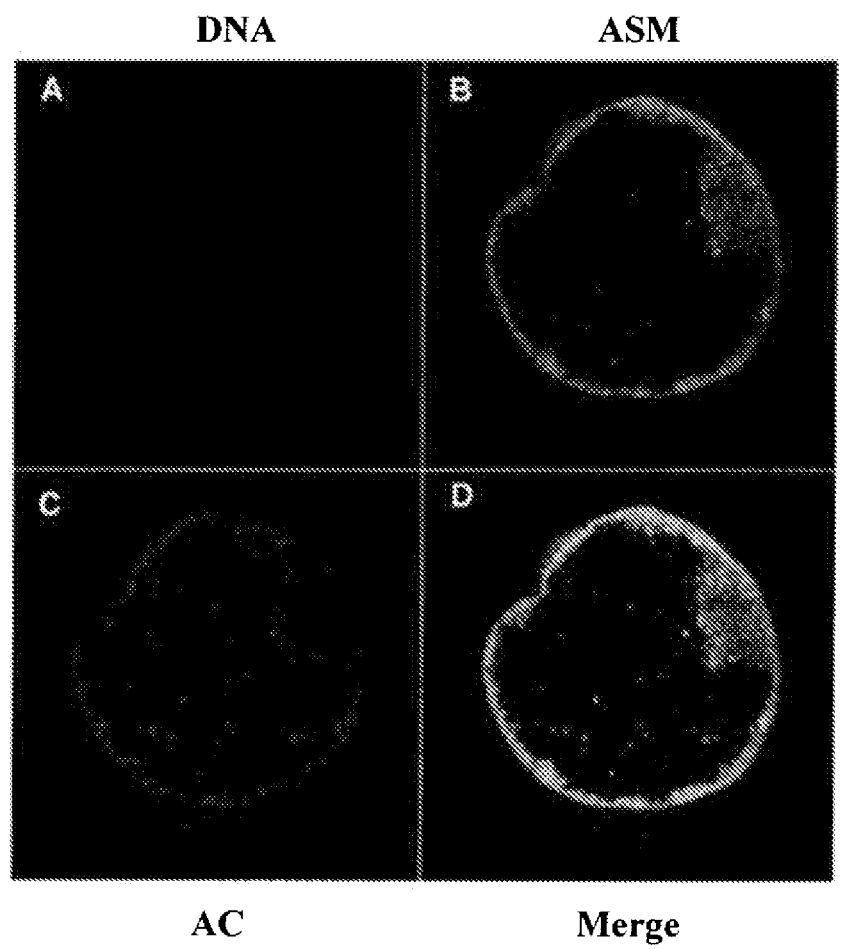
FIGS. 10A-D are stained images of denuded and fixed high grade human embryos. The embryos were incubated with the Hoechst DNA-specific fluorochrome 33342 (blue.

A first aspect of the present invention relates to a method of promoting the ex vivo survival of cells. This method involves providing one or more cells ex vivo and treating the one or more cells with acid ceramidase under conditions effective to promote survival of the one or more cells.

Acid ceramidase ("AC") is an enzyme that catalyzes the hydrolysis of ceramide to sphingosine and free fatty acid (Bernardo et al., "Purification, Characterization, and Biosynthesis of Human Acid Ceramidase," *J. Biol. Chem.* 270(19): 11098-102 (1995), which is hereby incorporated by reference in its entirety). Mature AC is a ~50 kDa protein composed of an α-subunit (~13 kDa) and a β-subunit (~40 kDa) (Bernardo et al., "Purification, Characterization, and Biosynthesis of Human Acid Ceramidase," *J. Biol. Chem.* 270(19):11098-102 (1995), which is hereby incorporated by reference in its entirety). It is produced through cleavage of the AC precursor protein (Ferlinz et al., "Human Acid Ceramidase: Processing, Glycosylation, and Lysosomal Targeting," *J. Biol. Chem.* 276 (38):35352-60 (2001), which is hereby incorporated by reference in its entirety), which is the product of the Asah1 gene (NCBI UniGene GeneID No. 427, which is hereby incorporated by reference in its entirety). The present invention demonstrates that AC promotes cell survival.

Cells whose survival can be promoted according to this aspect of the present invention include, without limitation, those that utilize the ceramidase apoptosis pathway, which includes a wide variety of cells (Obeid et al., "Programmed Cell Death Induced by Ceramide," *Science* 259:1769-71 (1993), which is hereby incorporated by reference in its entirety), e.g., hepatocytes (Arora et al., "Ceramide Induces Hepatocyte Cell Death Through Disruption of Mitochondrial Function in the Rat," *Hepatol.* 25:958-63 (1997), which is hereby incorporated by reference in its entirety), skin fibroblasts (Mizushima et al., "Ceramide, a Mediator of Interleukin 1, Tumour Necrosis Factor α, as Well as Fas Receptor Signalling, Induces Apoptosis of Rheumatoid Arthritis Synovial Cells," *Ann. Rheum. Dis.* 57:495-9 (1998), which is hereby incorporated by reference in its entirety), chondrocytes (MacRae et al., "Ceramide Inhibition of Chondrocyte Proliferation and Bone Growth Is IGF-I Independent," *J. Endocrinol.* 191(2):369-77 (2006), which is hereby incorporated by reference in its entirety), lung epithelium (Chan & Goldkorn, "Ceramide Path in Human Lung Cell Death," *Am. J. Respir. Cell Mol. Biol.* 22(4):460-8 (2000), which is hereby incorporated by reference in its entirety), erythrocytes (Lang et al., "Mechanisms of Suicidal Erythrocyte Death," *Cell. Physiol. Biochem.* 15:195-202 (2005), which is hereby incorporated by reference in its entirety), cardiomyocytes (Parra et al., "Changes in Mitochondrial Dynamics During Ceramide-induced Cardiomyocyte Early Apoptosis," *Cardiovasc. Res.* (2007), which is hereby incorporated by reference in its entirety), and lymphocytes (Gombos et al., "Cholesterol and Sphingolipids as Lipid Organizers of the Immune Cells' Plasma Membrane: Their Impact on the Functions of MHC Molecules, Effector T-lymphocytes and T-cell Death," *Immunol. Lett.* 104(1-2):59-69 (2006), which is hereby incorporated by reference in its entirety), eggs, embryos, neurons, sperm, synovial fibroblasts, and embryonic stem cells. Preferred cell types are eggs (fertilized or unfertilized), embryos, primary cells (e.g., neurons), sperm, synovial fibroblasts, and embryonic stem cells. Moreover, the ceramide apoptosis pathway appears to be conserved across mammalian species (Lee & Amoscato, "TRAIL and Ceramide," *Vitam. Horm.* 67:229-55 (2004); see also, Samadi, "Ceramide-induced Cell Death in Lens Epithelial Cells," Mol. Vis. 13:1618-26 (2007) (humans); Parra et al., "Changes in Mitochondrial Dynamics During Ceramide-induced Cardiomyocyte Early Apoptosis," *Cardiovasc. Res.* (2007) (rat); de Castro E Paula & Hansen, "Ceramide Inhibits Development and Cytokinesis and Induces Apoptosis in Preimplantation Bovine Embryos," *Mol. Reprod. Devel.*, DOI No. 10.1002/mrd.20841 (2007) (cows), each which is hereby incorporated by reference in its entirety). Therefore, it is expected that, for each of the cell types recited above, suitable cells include those of humans, monkeys, mice, rats, guinea pigs, cows, horses, sheep, pigs, dogs, and cats. In a preferred embodiment, this method is used to prolong the survival of eggs and/or embryos during in vitro fertilization procedures, facilitating the identification and selection of healthy embryos for reimplantation, especially for older human women and for veterinary breeding procedures.

Cells according to this aspect of the present invention can be provided by methods that will be apparent to the skilled artisan. By way of example, the cells can be obtained from an animal or from an existing ex vivo source (e.g., a tissue sample, a cell culture, etc.) using standard techniques. Treating cells ex vivo includes treating cells present in a homogeneous culture, as well as cells present in a heterogeneous culture (e.g., a tissue sample).

Acid ceramidases that can be used in this and all aspects of the present invention include, without limitation, those set forth in Table 1. In this and all aspects of the present invention (including the in vivo methods discussed below), the acid ceramidase can be homologous (i.e., derived from the same species) or heterologous (i.e., derived from a different species) to the one or more cells being treated.

TABLE 1

| Exemplary Acid Ceramidase Family Members | |
|---|---|
| *Homo sapiens* | |
| UniProt | Q13510, Q9H715, Q96AS2 |
| OMIM | 228000 |
| NCBI Gene | 427 |
| NCBI RefSeq | NP_808592, NP_004306 |
| NCBI RefSeq | NM_177924, NM_004315 |
| NCBI UniGene | 427 |
| NCBI Accession | Q13510, AAC73009 |
| *Mus musculus* | |
| UniProt | Q9WV54, Q3U8A7, Q78P93 |
| NCBI Gene | 11886 |
| NCBI RefSeq | NP_062708 |
| NCBI RefSeq | NM_019734 |

TABLE 1-continued

| Exemplary Acid Ceramidase Family Members | |
|---|---|
| NCBI UniGene | 11886 |
| NCBI Accession | AK151208, AK034204 |
| *Gallus gallus* | |
| UniProt | Q5ZK58 |
| NCBI Gene | 422727 |
| NCBI RefSeq | NP_001006453 |
| NCBI RefSeq | NM_001006453 |
| NCBI UniGene | 422727 |
| NCBI Accession | CAG31885, AJ720226 |
| *Pan troglodytes* | |
| NCBI Gene | 464022 |
| NCBI RefSeq | XP_519629 |
| NCBI RefSeq | XM_519629 |
| NCBI UniGene | 464022 |
| *Caenorhabditis elegans* | |
| UniProt | O45686 |
| IntAct | O45686 |
| NCBI Gene | 173120 |
| NCBI RefSeq | NP_493173 |
| NCBI RefSeq | NM_060772 |
| NCBI UniGene | 173120 |
| NCBI Accession | O45686, CAB05556 |
| *Danio rerio* | |
| UniProt | Q5XJR7 |
| NCBI Gene | 450068 |
| NCBI RefSeq | NP_001006088 |
| NCBI RefSeq | NM_001006088 |
| NCBI UniGene | 450068 |
| NCBI Accession | AAH83231, CB360968 |
| *Rattus norvegicus* | |
| UniProt | Q6P7S1, Q9EQJ6 |
| NCBI Gene | 84431 |
| NCBI RefSeq | NP_445859 |
| NCBI RefSeq | NM_053407 |
| NCBI UniGene | 84431 |
| NCBI Accession | AAH61540, AF214647 |

Treating according to this aspect of the present invention is carried out by contacting the cell(s) with the acid ceramidase, using methods that will be apparent to the skilled artisan.

In some embodiments, treating is carried out by introducing into the cell an acid ceramidase precursor protein, which is then converted into an active acid ceramidase protein by the cell. In particular, the AC precursor protein undergoes autoproteolytic cleavage into the active form (composed of α- and β-subunits). This is promoted by the intracellular environment, and based on highly conserved sequences at the cleavage site of AC precursor proteins across species, is expected to occur in most, if not all, cell types. Suitable acid ceramidase precursor proteins include those set forth in Table 1, supra. As will be apparent to the skilled artisan, the precursor protein could optionally be contained in a culture medium to which the cell is exposed. Embodiments in which the precursor protein is taken up by the cell of interest and converted into active acid ceramidase thereby, as well as embodiments in which the precursor protein is converted into acid ceramidase by a different cell or agent present in the culture medium, are both contemplated.

An approach for delivery of proteins or polypeptide agents (e.g., acid ceramidase, acid ceramidase precursor protein) involves the conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptide agents involves preparation of chimeric proteins according to U.S. Pat. No. 5,817,789 to Heartlein et al., which is hereby incorporated by reference in its entirety. The chimeric protein can include a ligand domain and the polypeptide agent (e.g., acid ceramidase, acid ceramidase precursor protein). The ligand domain is specific for receptors located on a target cell. Thus, when the chimeric protein is delivered to the cell or culture medium, the chimeric protein will adsorb to the targeted cell, and the targeted cell will internalize the chimeric protein.

In some embodiments, the acid ceramidase may be administered by introducing into the cell or culture medium a nucleic acid molecule that encodes the acid ceramidase (or acid ceramidase precursor protein, as described above) (JOSEPH SAMBROOK & DAVID W. RUSSELL, 1-3 MOLECULAR CLONING: A LABORATORY MANUAL (3d ed. 2001); SHORT PROTOCOLS IN MOLECULAR BIOLOGY (Frederick M. Ausubel et al. eds., 1999); U.S. Pat. No. 4,237,224 to Cohen & Boyer; each of which is hereby incorporated by reference in its entirety). Suitable nucleic acid molecules include those set forth in Table 1, supra. This includes introducing into the culture medium a cell that contains (and expresses) the nucleic acid molecule, and which secretes the acid ceramidase/acid ceramidase precursor protein into the culture medium.

Nucleic acid agents for use in the methods of the present invention can be delivered to a cell in a number of ways known in the art. For example, the nucleic acid can be contained within a vector, e.g., a vector that can be transferred to the cell(s) and provide for expression of the nucleic acid therein. Such vectors include chromosomal vectors (e.g., artificial chromosomes), non-chromosomal vectors, and synthetic nucleic acids. Vectors include plasmids, viruses, and phages, such as retroviral vectors, lentiviral vectors, adenoviral vectors, and adeno-associated vectors.

Nucleic acid agents can be transferred into the cell(s) using ex vivo methods, as will be apparent to the skilled artisan. For example, nucleic acids and vectors can be delivered to cells by physical means, e.g., by electroporation, lipids, cationic lipids, liposomes, DNA gun, calcium phosphate precipitation, injection, or delivery of naked nucleic acid.

As an alternative to non-infective delivery of nucleic acids as described above, naked DNA or infective transformation vectors can be used for delivery, whereby the naked DNA or infective transformation vector contains a recombinant gene that encodes the acid ceramidase/acid ceramidase precursor protein. The nucleic acid molecule is then expressed in the transformed cell.

The recombinant gene includes, operatively coupled to one another, an upstream promoter operable in the cell in which the gene is to be expressed and optionally other suitable regulatory elements (i.e., enhancer or inducer elements), a coding sequence that encodes the nucleic acid, and a downstream transcription termination region. Any suitable constitutive promoter or inducible promoter can be used to regulate transcription of the recombinant gene, and one of skill in the art can readily select and utilize such promoters, whether now known or hereafter developed. The promoter can also be specific for expression in the cell(s) whose survival is to be promoted. Tissue specific promoters can also be made inducible/repressible using, e.g., a TetO response element. Other inducible elements can also be used. Known recombinant techniques can be utilized to prepare the recombinant gene, transfer it into the expression vector (if used), and administer the vector or naked DNA to the cell. Exemplary procedures are described in SAMBROOK & RUSSELL, 1-3 MOLECULAR CLONING: A LABORATORY MANUAL (3d ed. 2001), which is hereby incorporated by reference in its entirety. One of skill in the art can readily modify these procedures, as desired, using known variations of the procedures described therein.

Any suitable viral or infective transformation vector can be used. Exemplary viral vectors include, without limitation, adenovirus, adeno-associated virus, and retroviral vectors (including lentiviral vectors).

Adenovirus gene delivery vehicles can be readily prepared and utilized given the disclosure provided in Berkner, "Development of Adenovirus Vectors for the Expression of Heterologous Genes," *Biotechniques* 6:616-29 (1988); Rosenfeld et al., "Adenovirus-mediated Transfer of a Recombinant α 1-antitrypsin Gene to the Lung Epithelium in Vivo," *Science* 252:431-434 (1991); PCT Publication No. WO/1993/007283 to Curiel et al.; PCT Publication No. WO/1993/006223 to Perricaudet et al.; and PCT Publication No. WO/1993/007282 to Curiel et al., each of which is hereby incorporated by reference in its entirety. Additional types of adenovirus vectors are described in U.S. Pat. No. 6,057,155 to Wickham et al.; U.S. Pat. No. 6,033,908 to Bout & Hoeben; U.S. Pat. No. 6,001,557 to Wilson et al.; U.S. Pat. No. 5,994,132 to Chamberlain & Kumar-Singh; U.S. Pat. No. 5,981,225 to Kochanek & Schniedner; U.S. Pat. No. 5,885,808 to Spooner & Epenetos; and U.S. Pat. No. 5,871,727 to Curiel, each of which is hereby incorporated by reference in its entirety.

Adeno-associated viral gene delivery vehicles can be constructed and used to deliver into cells a recombinant gene encoding a desired nucleic acid. The use of adeno-associated viral gene delivery vehicles in vitro is described in Chatterjee et al., "Dual-target Inhibition of HIV-1 in Vitro by Means of an Adeno-associated Virus Antisense Vector," *Science* 258:1485-8 (1992); Walsh et al., "Regulated High Level Expression of a Human γ-Globin Gene Introduced into Erythroid Cells by an Adeno-associated Virus Vector," *Proc. Nat'l Acad. Sci. USA* 89:7257-61 (1992); Walsh et al., "Phenotypic Correction of Fanconi Anemia in Human Hematopoietic Cells with a Recombinant Adeno-associated Virus Vector," *J. Clin. Invest.* 94:1440-8 (1994); Flotte et al., "Expression of the Cystic Fibrosis Transmembrane Conductance Regulator from a Novel Adeno-associated Virus Promoter," *J. Biol. Chem.* 268:3781-90 (1993); Ponnazhagan et al., "Suppression of Human α-Globin Gene Expression Mediated by the Recombinant Adeno-associated Virus 2-based Antisense Vectors," *J. Exp. Med.* 179:733-8 (1994); Miller et al., "Recombinant Adeno-associated Virus (rAAV)-mediated Expression of a Human γ-Globin Gene in Human Progenitor-derived Erythroid Cells," *Proc. Nat'l Acad. Sci. USA* 91:10183-7 (1994); Einerhand et al., "Regulated High-level Human β-Globin Gene Expression in Erythroid Cells Following Recombinant Adeno-associated Virus-mediated Gene Transfer," *Gene Ther.* 2:336-43 (1995); Luo et al., "Adeno-associated Virus 2-mediated Gene Transfer and Functional Expression of the Human Granulocyte-macrophage Colony-stimulating Factor," *Exp. Hematol.* 23:1261-7 (1995); and Zhou et al., "Adeno-associated Virus 2-mediated Transduction and Erythroid Cell-specific Expression of a Human β-Globin Gene," *Gene Ther.* 3:223-9 (1996), each of which is hereby incorporated by reference in its entirety.

Retroviral vectors which have been modified to form infective transformation systems can also be used to deliver a recombinant gene encoding a desired nucleic acid product into a target cell. One such type of retroviral vector is disclosed in U.S. Pat. No. 5,849,586 to Kriegler & Perez, which is hereby incorporated by reference in its entirety. Lentivirus vectors can also be utilized, including those described in U.S. Pat. No. 6,790,657 to Arya, and U.S. Patent Application Publication No. 2004/0170962 to Kafri et al. and U.S. Patent Application Publication No. 2004/0147026 to Arya, each of which is hereby incorporated by reference in its entirety.

Acid ceramidase treatment can be carried out as frequently as required and for a duration that is suitable to promote survival of the cell(s). For example, treatment can be carried out once, or multiple times.

The amount of acid ceramidase to be administered will, of course, vary depending upon the particular conditions. Generally, the acid ceramidase is administered to achieve an amount effective for improving survival of the cell(s). The amount required to obtain the desired effect may vary depending on the cell type, culture conditions, and duration for which it is desired that cell survival be promoted. Effective amounts can be determined empirically by those of skill in the art. For example, this may involve assays in which varying amounts of acid ceramidase are administered to cells in culture and the concentration effective for obtaining the desired result is calculated.

In a preferred embodiment, the acid ceramidase/acid ceramidase precursor protein is introduced into a culture medium, and the one or more cells are exposed to the culture medium before or after the acid ceramidase/acid ceramidase precursor protein is introduced.

Promoting survival according to this and all aspects of the present invention refers to any increase in the survival rate of the cell(s), including increasing the time it takes the cell(s) to die, and completely preventing the death of the cell(s).

A second aspect of the present invention relates to a method of promoting in vivo survival of one or more cells in a female mammalian subject. This method involves administering to the female mammalian subject acid ceramidase under conditions effective to promote survival of one or more cells in the female mammalian subject.

Mammals according to this aspect of the present invention include, without limitation, humans, monkeys, mice, rats, guinea pigs, cows, sheep, horses, pigs, dogs, and cats.

Cells according to this aspect of the present invention include those identified above. In a preferred embodiment, the one or more cells are eggs (fertilized or unfertilized).

It is predicted that acid ceramidase can protect the oocytes/embryos of women undergoing radiation and/or chemotherapy treatments, since these treatments are known to induce apoptosis in eggs via the ceramide pathway (Jurisicova et al., "Molecular Requirements for Doxorubicin-mediated Death in Murine Oocytes," *Cell Death Differ.* 13:1466-74 (2006); Tilly & Kolesnick, "Sphingolipids, Apoptosis, Cancer Treatments and the Ovary: Investigating a Crime Against Female Fertility," *Biochem. Biophys. Acta* 1585:135-8 (2002), each of which is hereby incorporated by reference in its entirety). Thus, in a preferred embodiment, the cells are eggs and the subject is a female human subjected to chemotherapy after administering the acid ceramidase.

An another preferred embodiment, the method according to this aspect of the present invention is carried out to prevent cell death of oocytes in vivo to enhance breeding efficiency of agricultural animals (e.g., horses, cows, sheep, pigs), domestic animals (e.g., dogs, cats, guinea pigs, hamsters), and/or laboratory animals (e.g., monkeys, mice, rats, guinea pigs, hamsters).

As discussed above with respect to ex vivo delivery, active acid ceramidase can be directly administered to the subject, and/or it may be delivered in the form of an acid ceramidase precursor protein and/or a nucleic acid encoding the acid ceramidase/acid ceramidase precursor protein. Exemplary proteins and nucleic acids include those set forth in Table 1, infra. The conjugated and chimeric proteins or polypeptide agents described above are also suitable in this aspect of the present invention.

As will be apparent to one of ordinary skill in the art, administering may be carried out using generally known methods. Exemplary methods are set forth below.

Administration can be accomplished either via systemic administration to the subject or via targeted administration to affected tissues, organs, and/or cells. The therapeutic agent (i.e., acid ceramidase, acid ceramidase precursor protein, nucleic acid encoding acid ceramidase/acid ceramidase precursor protein) may be administered to a non-targeted area along with one or more agents that facilitate migration of the therapeutic agent to (and/or uptake by) a targeted tissue, organ, or cell. Additionally and/or alternatively, the therapeutic agent itself can be modified to facilitate its transport to (and uptake by) the desired tissue, organ, or cell, as will be apparent to one of ordinary skill in the art. Preferred target tissues in the case of promoting survival of eggs include ovarian tissue and uterine tissue.

Any suitable approach for delivery of the agents can be utilized to practice this aspect of the present invention. Typically, the therapeutic agent will be administered to a patient in a vehicle that delivers the therapeutic agent(s) to the target cell, tissue, or organ.

Exemplary routes of administration include, without limitation, by intratracheal inoculation, aspiration, airway instillation, aerosolization, nebulization, intranasal instillation, oral or nasogastric instillation, intraperitoneal injection, intravascular injection, topically, transdermally, parenterally, subcutaneously, intravenous injection, intra-arterial injection (such as via the pulmonary artery), intramuscular injection, intrapleural instillation, intraventricularly, intralesionally, by application to mucous membranes (such as that of the nose, throat, bronchial tubes, genitals, and/or anus), or implantation of a sustained release vehicle.

Typically, the therapeutic agent will be administered as a pharmaceutical formulation that includes the therapeutic agent and any pharmaceutically acceptable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of therapeutic agent together with the adjuvants, carriers and/or excipients. The amount of active compound in such therapeutically useful compositions is such that a suitable dosage unit will be obtained.

The agents may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of the agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient(s), sucrose as a sweetening agent, methyl and propylparabens as preservatives, a dye, and flavoring such as cherry or orange flavor.

The agents may also be administered parenterally. Solutions or suspensions of the agent can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents according to this aspect of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form.

Exemplary delivery devices include, without limitation, nebulizers, atomizers, liposomes (including both active and passive drug delivery techniques) (Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987); Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al.; Wolff et al., "The Use of Monoclonal Anti-Thy1 IgG1 for the Targeting of Liposomes to AKR-A Cells in Vitro and in Vivo," *Biochim. Biophys. Acta* 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of the therapeutic agent to the desired organ, tissue, or cells in vivo to effect this aspect of the present invention.

Administration can be carried out as frequently as required and for a duration that is suitable to provide effective promotion of cell survival. For example, administration can be carried out with a single sustained-release dosage formulation or with multiple daily doses.

The amount to be administered will, of course, vary depending upon the treatment regimen. Generally, an agent is administered to achieve an amount effective for improving survival of the cell(s). Thus, a therapeutically effective amount can be an amount which is capable of at least partially preventing apoptosis of the cell(s), including delaying the onset of cell death. The dose required to obtain an effective amount may vary depending on the agent, formulation, cell type, the duration for which it is desired that cell survival be promoted, and individual to whom the agent is administered.

Determination of effective amounts may also involve in vitro assays in which varying doses of agent are administered to cells in culture and the concentration of agent effective for promoting cell survival is determined in order to calculate the concentration required in vivo. Effective amounts may also be based on in vivo animal studies. A therapeutically effective amount can be determined empirically by those of skill in the art.

A third aspect of the present invention relates to a kit for promoting ex vivo primary cell survival. The kit includes a cell culture medium and an acid ceramidase.

Suitable cell culture media according to this aspect of the present invention include, without limitation, M2 for oocytes and embryos, RPMI and DMEM for many primary cells (including fibroblasts), and B27 for neurons.

The acid ceramidase according to this aspect of the present invention includes those identified above. The acid ceramidase can be in protein form, and/or in the form of a nucleic acid molecule encoding acid ceramidase.

The kit according to this aspect of the present invention may optionally include one or more cells in the culture medium, including any of the cells identified above. As will the apparent to the skilled artisan, where more than one cell is included, the cells can be homogeneous (i.e., the same cell type from the same species) or heterogeneous (i.e., different cell types and/or cells from different species).

A fourth aspect of the present invention relates to a method of predicting in vitro fertilization outcome. This method involves providing a sample of serum or follicular fluid from a female subject. The sample is screened for acid ceramidase activity level, and the acid ceramidase activity level is correlated to a prediction of the outcome of in vitro fertilization for the female subject.

The sample may be provided using methods that will be apparent to the skilled artisan. For example, serum can be obtained by standard blood draw. Follicular fluid is obtained during oocyte retrieval during assisted fertilization.

Suitable subjects according to this aspect of the present invention include those identified above. In a preferred embodiment, the subject is a human.

The sample can be screened for acid ceramidase activity by methods that will be apparent to the skilled artisan. Suitable methods include, for example, AC activity assays (Eliyahu et al., "Acid Ceramidase Is a Novel Factor Required for Early Embryo Survival," *FASEB J.* 21(7):1403-9 (2007), which is hereby incorporated by reference in its entirety), western blotting to determine the relative amount of AC present in the sample (where a higher amount of AC protein correlates to a higher AC activity level) (Eliyahu et al., "Acid Ceramidase Is a Novel Factor Required for Early Embryo Survival," *FASEB J.* 21(7):1403-9 (2007), which is hereby incorporated by reference in its entirety), and RIA (Ferlinz et al., "Human Acid Ceramidase: Processing, Glycosylation, and Lysosomal Targeting," *J. Biol. Chem.* 276(38):35352-60 (2001), which is hereby incorporated by reference in its entirety).

It is expected that females with low AC in serum and/or follicular fluid have a higher percentage of apoptotic eggs, and thus a poorer predicted outcome for in vitro fertilization. Therefore, the AC activity level of the sample can be correlated to the predicted outcome by comparing that level to a standard level. The standard can be determined using population data from females of various ages (see, for example, Example 14, infra).

The present invention may be further illustrated by reference to the following examples.

EXAMPLES

Example 1

Mouse Egg and Embryo Collection

All experiments involving animals were approved by, and performed in strict accordance with, the guidelines of the appropriate institutional animal care and use committees. Seven to 8-week-old 129-SV/IMJ and C57-Black/6 female mice (Jackson Labs, Bar Harbor, Me.) were superovulated with 10 international units ("IU") of pregnant mares' serum gonadotropin ("PMSG;" Syncro-part, Sanofi, France), followed by 10 IU of human chorionic gonadotropin ("hCG;" Sigma, St. Louis, Mo.) 48 hours later. Mature and old MII stage eggs were collected from the oviducal ampullae 16 hours or 46 hours, respectively, after injection of hCG. Cumulus cells were removed by a brief exposure to 400 IU/ml of highly purified hyaluronidase (H-3631; Sigma) in Todd-Hewitt medium (Eliyahu & Shalgi, "A Role for Protein Kinase C During Rat Egg Activation," *Biol. Reprod.* 67:189-95 (2002), which is hereby incorporated by reference in its entirety). For 2-cell embryo collection, superovulated females were caged with males of proven fertility and sacrificed 46 hours after injection of hCG. Embryos were isolated from the oviducal ampullae and cultured at 37° C. in a humidified atmosphere of 5% $CO_2$ and 95% air.

Example 2

Single Cell Long Nested PCR Genotyping

DNA from individual embryos was subjected to PCR amplification using a mixture of two sets of long and short (nested) primers. Long$^{1st}$ and short$^{2nd}$ PCR amplification of the wild-type Asah1 allele was performed using forward and reverse primers (5'-ACCCAGGTTCCATCGTTGCA-CATTTCATC-3' (SEQ ID NO: 1), 5'-ATGCCACATGG-GAATACTGTCCAAAGCAGAA-3' (SEQ ID NO: 2), and 5'-CACACAAACACATGTATGTGCACACGTGAA-3' (SEQ ID NO: 3), 5'-GCTGCCCTGGAACTCACTCACTCT-3' (SEQ ID NO: 4)) to produce ~9-kb and 180-bp DNA fragments, respectively. Amplification of the mutated Asah1 allele using forward and reverse primers (5'-ATGCCA-CATGGGAATACTGTCCAAAGCAGAA-3 (SEQ ID NO: 2)', 5'-GAGGAGTAGAAGGTGGCGCGAAGGGG-3' (SEQ ID NO: 5), and 5'-GCTGCCCTGGAACTCACTCACTCT-3' (SEQ ID NO: 4), 5'-GGTGGATGTGGAATGTGTGCGA-3' (SEQ ID NO: 6)) produced ~7-kb and 255-bp DNA fragments, respectively.

Example 3

Western Blot Analysis

Eggs and embryos were subjected to lysis in buffer containing 50 mM Tris-HCL, 150 mM NaCl, 2 mM EDTA, 1% NP-40, 1 mM Vanadate, 5 mM Naf, and 10 µg/ml aprotinine (pH 7.4). Proteins were separated by SDS-PAGE using 10% or 12% pre-cast Nupage Bis/Tris gels under reducing conditions and MES running buffer (Invitrogen), and transferred onto a nitrocellulose membrane (Amersham Biosciences) using a semi-dry transfer apparatus (BioRad) and Nupage-MOPS transfer buffer. For immunoblot analysis, blots were blocked with TBS/Tween containing 5% dry milk, and then were incubated with Goat IgG against acid ceramidase ("AC") (specific for the β-subunit). Bound antibodies were recognized by secondary antibodies conjugated to horseradish peroxidase. Detection was performed by an enhanced chemiluminescence detection reagent (Amersham Biosciences). Approximate molecular masses were determined by comparison with the migration of pre-stained protein standards (BioRad).

Example 4

Acid Ceramidase Activity Assay

Eggs were subjected to lysis in 0.25% sucrose solution. Total cell extracts were incubated for 22 hours at 37° C. with 0.1 ng/ml BODIPY-conjugated C12-ceramide in 0.1M citrate/phosphate buffer (pH 4.5), 150 mM NaCl, 0.05% BSA, and 0.1% Igepal CA-630. After the reactions were complete, 5 µl of the assay mixtures were removed and added into 95 µl of ethanol, mixed, and then centrifuged for 5 minutes at 10,000× g. The supernatants were then transferred to a Waters glass sampling vial, and 5 µl (2.5% of the original reaction mixture) were auto-sampled by a WIPS 712 (Waters) autosampler onto a high performance liquid chromatograph equipped with a reverse-phase column (BetaBasic-18, 4.6× 30 mm, Keystone Scientific Inc., Bellefonte, Pa.), and eluted isocratically with methanol/water (95:5 v/v) at a flow rate of 1 ml/min. Fluorescence was quantified using a Waters 474 fluorescence detector set to excitation and emission wavelengths of 505 nm and 540 nm, respectively. The undigested substrate (i.e., BODIPY-conjugated C12-ceramide) and product (i.e. fatty acid) peaks were identified by comparing their retention times with standards, and the amount of product was calculated using a regression equation that was established from a standard curve using BODIPY-conjugated C12 fatty acid.

Example 5

Immunohistochemistry

Eggs were isolated and fixed in 3% paraformaldehyde. Zonae pellucidae ("ZP") were removed post-fixation by pronase (Sigma), and the ZP free eggs were permeabilized by NP-40. The eggs were then incubated with different primary and secondary antibodies (Eliyahu & Shalgi, "A Role for Protein Kinase C During Rat Egg Activation," *Biol. Reprod.* 67:189-95 (2002), which is hereby incorporated by reference in its entirety). The fluorescent reagents were visualized and photographed with a Ziess confocal laser-scanning microscope. For apoptosis detection, live 2-cell embryos were labeled using an Annexin V Apoptosis Detection Kit (Santa Cruz Biotechnology, Inc.).

Example 6 mRNA Quantification by Polymerase Chain Reaction

Total mRNA was extracted from equal numbers of eggs and embryos, and reverse-transcribed according to the manufacturer's instruction (Invitrogen). Mac990 (5'-TTACCGCA-GAACACCGGCC-3' SEQ ID NO: 7)) and mac1137r (5'-TTGACCTTTGGTAACATCCATC-3' (SEQ ID NO: 8)) were used for murine AC PCR amplification with QuantiTect SYBR Green PCR kit (QIAGEN). Changes in AC mRNA levels in old eggs and 2-cell embryos were assessed relatively to the level of AC mRNA in young eggs using the formulas $2^{\wedge}(Ct_{young}-Ct_{old})$ and $2^{\wedge}(Ct_{young}-Ct_{2\text{-}cell\ embryo})$, respectively. Housekeeping proteins actin beta, glyceraldehyde-3-phosphate dehydrogenase, and ribosomal protein S11 (RPS 11) were used as internal controls for embryonic mRNA expression.

Example 7

Data Presentation and Statistical Analysis

All experiments were independently replicated at least three times with different mice. The combined data from the replicate experiments were subjected to a t-test analysis, and results were considered statistically significant at P<0.005. Graphs represent the mean±s.e.m. of combined data from the replicate experiments. Representative photomicrographs are presented for the egg morphology, Annexin V labeling, and immunohistochemistry assays.

Example 8

Asah1−/− Mouse Embryos are Formed, but Die During the 2-4-Cell Transition

To gain insights into the pathological mechanism underlying the lethal phenotype of Asah1−/− mice, a single-cell, long nested ("SCLN") PCR genotyping method was developed. This technique allowed for the genotyping of individual embryos immediately after fertilization. Two- to 8-cell stage embryos were collected from Asah1+/− intercrosses 36-60 hours after human chorionic gonadotropin injection, and cultured in M2 media. DNA was obtained from single embryos and subjected to SCLN PCR amplification using a mixture of long and nested PCR primers, as described in Examples 1-2. Genotyping of 196 embryos from these intercrosses revealed that Asah1−/− embryos could be formed, as shown in FIG. 1. However, no Asah1−/− embryos were identified beyond the 2-cell stage, as shown in Table 2, suggesting that the lack of AC activity led to embryo death during the 2- to 4-cell transition. Notably, more Asah1+/− embryos were identified at the 4- to 8-cell stage than predicted, i.e., the predicted wild-type to heterozygote ratio was 1:2, while the actual ratio was ~1:2.8, as shown in Table 2. This was attributed to the fact that older Asah1+/− male mice were used to produce these embryos, and that mutant sperm from such mice have a fertilization advantage compared to wild-type sperm.

TABLE 2

Embryo Genotyping Results.

| | +/+ | +/− | −/− | Total |
|---|---|---|---|---|
| 2-cell embryos | 40 | 72 | 32 | 143 |
| 4-8-cell embryos | 14 | 39 | 0 | 53 |

2-8-cell embryos from Asah1−/− intercrosses were subjected to genotyping by SCLN PCR. The data represent genotyping of 100% of the embryos obtained from 8 female mice.

Example 9

Asah1−/− Mouse Embryos Undergo Apoptotic Death During the 2-Cell Stage

Ceramide-mediated signaling often leads to apoptosis (Spiegel et al., "Signal Transduction Through Lipid Second Messengers," *Curr. Opin. Cell. Biol.* 8:159-67 (1996), which is hereby incorporated by reference in its entirety). Therefore, one consequence of inactivating the Asah1 gene might be the increase of ceramide in embryos, leading to cell cycle arrest or apoptosis (Hannun, "Function of Ceramide in Coordinating Cellular Responses to Stress," *Science* 274:1855-9 (1996); Spiegel et al., "Signal Transduction Through Lipid Second Messengers," *Curr. Opin. Cell. Biol.* 8:159-67 (1996), which are hereby incorporated by reference in their entirety). It has been shown that ceramide levels in eggs are increased during in vivo and in vitro aging (Perez et al., "A Central Role for Ceramide in the Age-related Acceleration of Apoptosis in the Female Germline," *FASEB J.* 19:860-2 (2005), which is hereby incorporated by reference in its entirety). These data support the conclusion that AC plays an important role in egg/embryo survival by removal of ceramide.

To further investigate the involvement of AC during development, and to characterize the mechanism leading to the death of Asah1−/− embryos, the possibility of apoptotic death was assessed by Annexin V staining (Chan et al., "Plasma Membrane Phospholipid Asymmetry Precedes DNA Fragmentation in Different Apoptotic Cell Models," *Histochem. Cell Biol.* 110:553-8 (1998), which is hereby incorporated by reference in its entirety). To perform this analysis, 86 live 2-cell embryos from Asah1+/− intercrosses were collected and designated numbers. Each embryo was examined independently for apoptotic morphology and Annexin V binding using laser-scanning confocal microscopy, and then genotyped by SCLN PCR. The outcome of these analyses revealed that all of the Asah1−/− embryos had apoptotic morphology, as shown in FIGS. 2D and 2F, and positive Annexin V staining, as shown in FIGS. 2E-F, while wild-type embryos had normal morphology, as shown in FIGS. 2A and 2C, and no Annexin V staining except of the apoptotic polar body, as shown in FIGS. 2B-C. As shown in Table 3, the percentages of apoptotic wild-type (11%) and heterozygous (5%) embryos were negligible compared to Asah1−/− embryos (100%) (t-test, P<0.00001).

TABLE 3

Asah1−/− Embryos Undergo Apoptotic Death During the 2-Cell Stage.

| | +/+ | +/− | −/− | Total |
|---|---|---|---|---|
| 2-cell embryos (genotype) | 27 | 42 | 17 | 86 |
| Annexin V positive and/or abnormal morphology | 3 ± 1 (11%) | 2 ± 1 (5%) | 17 ± 0 (100%) | 22 |

The data represent analysis of 100% of the embryos obtained from 4 female mice.

Thus, these findings reveal that the absence of functional AC causes apoptotic death during the 2-cell stage, and provides direct in vivo evidence that AC activity is essential for the 2- to 4-cell transition. This developmental period marks the beginning of embryonic genome activation.

Example 10

Acid Ceramidase Expression in Unfertilized Mouse Oocytes

Since AC appears to be required for the earliest stages of embryo development, it was hypothesized that the enzyme must be provided to newly formed embryos by the donor egg before embryonic genome activation ("EGA") in order for these embryos to survive. To examine this hypothesis, cell extracts were prepared from 400 pooled, unfertilized MII eggs (collected 16 hours after hCG injection), and analyzed by western blot to identify the AC protein. As can be seen in FIG. 3, the AC precursor protein (55 kDa) and β-subunit (40 kDa) are expressed in the egg before fertilization. The presence of the processed β-subunit indicates that some of the AC was likely to be active. Cell extracts were therefore prepared from an additional 65 pooled, unfertilized eggs, and subjected to AC activity assays. As shown in FIG. 3, these analyses revealed a high enzymatic activity (t-test, $p<0.005$), confirming the western blot results.

To obtain information about the subcellular location of AC in eggs, immunohistochemistry was performed using anti-AC specific antibodies combined with anti-LAMP1 staining for late endosome/lysosome detection. The fluorescence distribution of the AC and LAMP-1 signals was visualized at the equator and cortex of the egg, and photographed with a Ziess confocal laser-scanning microscope, as shown in FIGS. 4A-G. These studies reveal that AC is localized mainly at the egg cortex, as shown in FIGS. 4A and 4D, and co-localizes with LAMP-1 in the late endosomes/lysosomes, as shown in FIGS. 4B and 4D-F.

Example 11

Normal Mouse Embryos Express Acid Ceramidase at Embryonic Genome Activation

The death of AC-deficient embryos during the 2-cell stage implies that in normal embryos AC gene expression occurs as early as the EGA to sustain survival. To confirm this hypothesis, changes in AC mRNA levels in old, unfertilized MII eggs and 2-cell embryos (both collected 46 hours after hCG injection) were assessed relative to the levels in young, unfertilized eggs (collected 16 hours after hCG injection). Total mRNA was extracted from equal numbers of eggs and embryos, and quantified using the QuantiTect SYBR Green PCR kit (see Example 6). Housekeeping proteins β-actin, glyceraldehyde-3-phosphate dehydrogenase, and ribosomal protein S11 were used as internal controls for embryonic mRNA expression. As shown in FIG. 5, of AC mRNA decreased significantly in old versus young unfertilized eggs (t-test, $p<0.0003$). This would predictably result in ceramide increase and apoptotic cell death. On the other hand, as shown in FIG. 5, AC mRNA levels were enhanced in fertilized, healthy 2-cell embryos (t-test, $p<0.0005$), suggesting AC gene activation during EGA.

To confirm the PCR findings, AC protein levels were assessed in 140 pooled unfertilized eggs in comparison to 140 2-cell embryos by western blot analysis, followed by densitometric analysis, using actin as a control. The level of AC precursor was increased in 2-cell embryos as compared to unfertilized eggs, consistent with the mRNA findings. As shown in FIG. 5, ribosomal protein S11, one of the first genes expressed immediately after fertilization, was also used as a control to mark the initiation of EGA. Glyceraldehyde-3-phosphate dehydrogenase was used as a negative control, as shown in FIG. 5. Overall, the fact that AC was expressed in young eggs before fertilization and AC levels decreased during the aging process, together with the fact that there was enhanced AC expression during EGA, highlights the importance of this enzyme for embryo survival. These data show that embryonic AC gene expression is initiated during the 2-cell stage.

Discussion of Examples 1-11

During normal development eggs proceed to apoptosis unless fertilization occurs. Among the complex regulatory pathways that are needed to control this delicate balance between death and survival, sphingolipid signaling is an important component. Indeed, ceramide accumulation in aging eggs has been shown to result in apoptosis, and the anti-apoptotic lipid, sphingosine-1-phosphate ("S1P"), can counteract the effects of ceramide and promote egg survival (Perez et al., "A Central Role for Ceramide in the Age-related Acceleration of Apoptosis in the Female Germline," *FASEB J.* 19:860-2 (2005); Miao et al., "Cumulus Cells Accelerate Aging of Mouse Oocytes," *Biol. Reprod.* 73:1025-1031 (2005), which are hereby incorporated by reference in their entirety). Other physiological changes in unfertilized eggs and early embryos, including $Ca^{2+}$ oscillations, are also important components of this regulatory decision. Upon fertilization, young, healthy eggs must supply sufficient anti-apoptotic proteins and mRNA to newly formed embryos to overcome the default apoptosis pathway. Afterwards, the newly formed embryo must supply these factors through expression of its own genome at embryonic genome activation ("EGA"). In the mouse, EGA begins during the 2-cell stage (Flach et al., "The Transition from Maternal to Embryonic Control in the 2-Cell Mouse Embryo," *EMBO J.* 1:681-6 (1982), which is hereby incorporated by reference in its entirety), whereas in humans the major activation event occurs between the 4- and 8-cell stages (Telford et al., "Transition from Maternal to Embryonic Control in Early Mammalian Development: A Comparison of Several Species," *Mol. Reprod. Dev.* 26:90-100 (1990), which is hereby incorporated by reference in its entirety). Although anti-apoptotic factors should be among the genes/proteins expressed at EGA, very few such factors have been identified to date.

Consistent with prior evidence showing that increased ceramide levels in aging eggs leads to apoptosis (Perez et al., "A Central Role for Ceramide in the Age-related Acceleration of Apoptosis in the Female Germline," *FASEB J.* 19:860-2 (2005); Miao et al., "Cumulus Cells Accelerate Aging of Mouse Oocytes," *Biol. Reprod.* 73:1025-1031 (2005), which are hereby incorporated by reference in their entirety), it was hypothesized that AC, an enzyme responsible for the hydrolysis of ceramide and the production of sphingosine (the precursor of S1P), might be an essential factor required for embryo survival. It was also hypothesized that in the absence of AC activity, ceramide levels in 2-4 cell AC knockout embryos would increase, leading to apoptosis. While it is not possible to accurately quantify ceramide in individual embryos due to the limited sensitivity of the available techniques and/or the fact that these techniques preclude subsequent genotyping (e.g., immunohistochemistry), the present studies clearly show that embryo-derived AC is one of the first proteins expressed during the 2-cell stage of development in mice, and that its activity is necessary for the subsequent expression of the normal developmental program. In the absence of this activity, embryos undergo apoptotic death.

Additionally, AC activity is not only essential during embryonic development, but during postnatal life as well. In humans, reduced AC activity leads to the lipid storage disease Farber Lipogranulomatosis ("FD"). FD is an extremely rare and fatal lipid storage disorder, and at least two cases of fetal death have been reported (Kattner et al., "Hydrops fetalis:

Manifestation in Lysosomal Storage Diseases Including Farber Disease," *Eur. J. Ped.* 156:292-5 (1997); Van Lijnschoten et al., "Intrauterine Fetal Death Due to Farber Disease: Case Report," *Pediatr. Dev. Pathol.* 3:597-602 (2000), which are hereby incorporated by reference in their entirety). Mutation analysis carried out on surviving FD patients has shown that subtle point mutations account for most of the abnormalities, rather than large gene deletions, rearrangements, or frameshift mutations, which are likely to cause complete loss-of-function. Indeed, even these subtle point mutations often lead to a severe clinical condition (Moser et al., "Acid Ceramidase Deficiency: Farber Lipogranulomatosis," in THE METABOLIC & MOLECULAR BASIS OF INHERITED DISEASE 3573-88 (Charles R. Scriver et al. eds., $8^{th}$ ed. 2001), which is hereby incorporated by reference in its entirety), providing further evidence that AC activity is essential for normal postnatal development. The present Examples demonstrate that mice homozygous for the complete loss-of-function Asah1 allele undergo apoptotic death at the 2-cell stage. These findings indicate that complete loss-of-function mutations in FD individuals would lead to early embryonic lethality, and are consistent with the fact that only patients with subtle point mutations survive.

Historically, AC was classified as a "lysosomal enzyme" because of the appearance of lipid storage vacuoles in FD patients that were reminiscent of lysosomes, as well as the enhanced in vitro activity at acidic pH. The present Examples document the sub-cellular location of AC in unfertilized eggs, and shows the presence of this protein both inside and outside of lysosomes. Although several reports have suggested that ceramide produced in lysosomes does not participate in cell signaling (e.g., Ohanian & Ohanian, "Sphingolipids in Mammalian Cell Signaling," *Cell. Mol. Life Sci.* 58:2053-68 (2001), which is hereby incorporated by reference in its entirety), it is important to recognize that AC may contribute to the hydrolysis of non-lysosomal, as well as intra-lysosomal, ceramide pools. In fact, the related lipid hydrolase, acid sphingomyelinase, can hydrolyze sphingomyelin in both lysosomal and non-lysosomal compartments, and rapidly relocates to the cell surface following various stimuli (Ohanian & Ohanian, "Sphingolipids in Mammalian Cell Signaling," *Cell. Mol. Life Sci.* 58:2053-68 (2001), which is hereby incorporated by reference in its entirety).

The development of a single-cell, PCR genotyping method for AC could potentially facilitate pre-implantation diagnosis of FD embryos for at-risk couples. While this method would have to be adapted from mice to humans, this should not be problematic, since the genes are highly conserved. Furthermore, based on the present findings, physicians could potentially use AC to prolong egg/embryo survival during IVF procedures, facilitating the identification and selection of healthy embryos for re-implantation, especially for older women. In conclusion, these data reveal a new and important role for AC in the earliest stages of mammalian embryogenesis, and suggest that this enzyme and/or gene may be used to facilitate egg/embryo survival in vitro and/or in vivo.

Example 12

Acid Ceramidase Prolongs the Lifespan of Mouse Oocytes

MII oocytes were collected from superovulated female mice and placed into a fresh media. Oocytes were incubated for 24 hours in a humidified incubator at 37° C. in the absence or presence of acid ceramidase. The oocytes were fixed and stained with Hoechst for DNA labeling. The morphology and DNA staining were visualized using laser-scanning confocal microscopy. As shown in FIGS. 6A-B, addition of acid ceramidase to the incubation media prolonged the lifespan of the oocytes.

MII oocytes were incubated for 24 hours in M2 media (with or without AC), media collected from a CHO cell line that does not express AC, or media collected from a CHO cell line that stably expresses and secretes AC. As shown in FIG. 7, the rate of apoptosis was significantly reduced in oocytes incubated in media that contained AC.

Example 13

Acid Ceramidase Expression and Localization in Human Oocytes and Early Embryos

Oocytes and embryos from women scheduled for in vitro fertilization with intracyctoplasmic sperm injection were collected ~32 hours (oocytes) or 3-5 days (embryos) after injection of luteinizing hormone.

Co-immunohistochemistry assays were performed to detect the localization and possible interaction between AC and lysosome associated membrane protein ("LAMP") (a lysosomal enzyme marker) during human oocyte maturation. Oocytes were triple labeled for AC protein, cellular DNA, and LAMP, and examined for co-localization by immunofluorescence confocal microscopy. As shown in FIGS. 8A-H, AC is localized mainly in the cortex and membrane, and co-localizes with LAMP, during both the germinal vesicle stage (FIGS. 8A-D) and the germinal vesicle break down stage (FIGS. 8E-H). In addition, AC is co-localized with the GV membrane break down, as shown in FIGS. 8E-H. As shown in FIGS. 8I-L, AC protein is co-localized with LAMP and with DNA during the MI stage. During the MII stage, AC is homogenously distributed throughout the cytosol with a marked localization at the membrane and cortex, and co-localization in the spindle, as shown in FIGS. 8M-P). These data clearly show changes in the developmental pattern of AC expression during human egg maturation. This is the first known study that demonstrates that AC is expressed in human oocytes.

Co-immunohistochemistry assays were also performed to detect the localization and possible interaction between AC and acid sphingomyelinase ("ASM"), a related enzyme that hydrolyzes sphingomyelin into ceramide, during early embryo development. Embryos were triple labeled for AC protein, cellular DNA, and ASM, and examined for co-localization by immunofluorescence confocal microscopy. As shown in FIGS. 9A-D and FIGS. 10A-D, AC is localized in the embryonic fluid and co-localizes with ASM mainly in the inner and outer cell mass. Moreover, high-grade embryos (FIGS. 10A-D) demonstrate higher expression of AC in the embryonic fluid then do low-grade embryos (FIGS. 9A-D). Thus, high-grade embryos would be expected to have lower ceramide levels and higher SIP levels than low-grade embryos, and therefore a higher survival rate (due to a lower incidence of apoptosis).

Example 14

Acid Ceramidase Expression and Activity in Human Follicular Fluid

Figure 11:
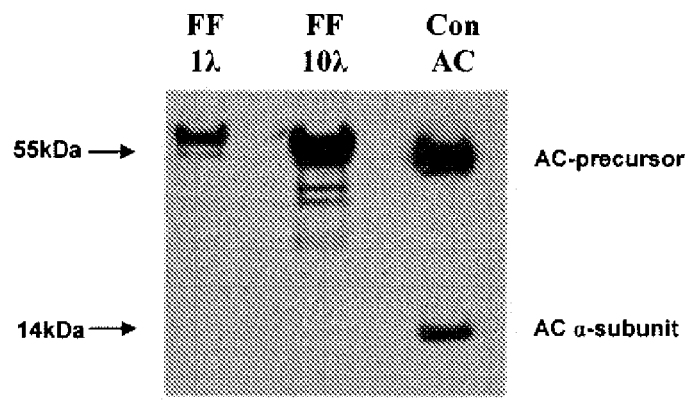
FIG. 11 is a western blot of human follicular fluid samples using antibodies against the AC precursor protein or the AC α-subunit. A 1 μl sample was loaded onto lane 1 ("FF 1λ") and a 10 μl sample was loaded onto lane 2 ("FF 10λ"). Pure AC was loaded onto lane 3 as a control ("Con AC").

Human follicular fluid samples from oocytes assigned for in vitro intracyctoplasmic sperm injection were collected during oocyte retrieval. Western blot analysis was used to evaluate the total amount of AC in the follicular fluid. Proteins were separated by SDS-PAGE. A monoclonal mouse anti-human AC IgM was used to detect the AC precursor protein (55 kDa). As shown in FIG. 11, the AC precursor protein is highly expressed in human follicular fluid.

Figure 12:
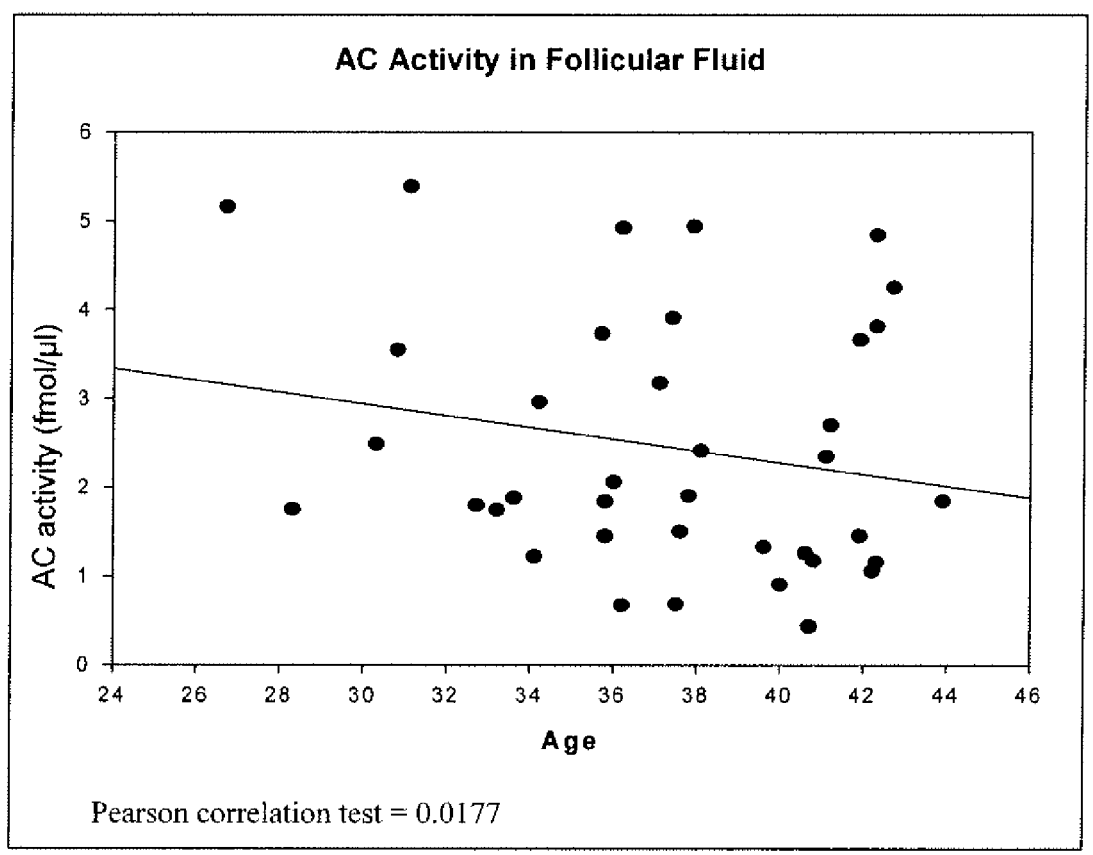
FIG. 12 is a plot of AC activity in human follicular fluid as a function of maternal age (in years).

An in vitro activity assay was used to evaluate the activity of AC in human follicular fluid. Follicular fluid samples were incubated under acidic conditions for 22 hours at 37° C. with BODIPY conjugated C12-ceramide, and then analyzed by HPLC. The results of this activity assay were correlated with patient age using the Pearson correlation test. As shown in FIG. 12, there is a trend towards a decrease in AC activity with increasing age. This suggests that the measurement of AC in follicular fluid can be used as a marker for reproductive aging.

Example 15

Acid Ceramidase Prolongs the Life Span of Human Oocytes

Immature oocytes from women scheduled for in vitro intracyctoplasmic sperm injection were collected ~24 hours after LH injection and transferred into Quinns Advantage Cleavage Medium with 5% HAS, supplemented with or without human AC, ~32 hours after LH injection. Oocytes were denuded and fixed 24 hours after culture in vitro in 50 µl drop under oil. Oocyte quality was evaluated based on membrane and cytoplasm morphology, and DNA appearance and integrity. DNA integrity was evaluated using the TUNEL staining assay, which detects fragmented DNA, an indicator of apoptosis.

As shown FIG. 13A, oocytes from the control group were more sensitive to fixation, and exhibited membrane blebbing and the beginning of cytoplasm fragmentation, which are indicative of apoptosis. In contrast, oocytes that were cultured in the presence of AC had a stronger membrane and looked intact and smooth after fixation, as shown in FIG. 13B. Morphology of the metaphase plate was defective in four out of six MII oocytes in the control group. As shown in FIG. 14A, oocytes cultured without AC have visible, condensed chromatin (presumably due to spindle disruption), an early sign of apoptosis. In contrast, six out of seven oocytes cultured in presence of AC conserved a proper metaphase plate and clearly distinguishable chromosomes (i.e., no condensed chromatin). See FIGS. 14A-D for an illustration of DNA condensation. This suggests that oocytes cultured without AC are more susceptible to apoptosis than oocytes cultured with AC. TUNEL staining was carried out to more directly confirm this. As shown in FIGS. 15A-B, oocytes in the control group had a greater extent of DNA fragmentation, presented by stronger TUNEL staining, while oocytes that were cultured in the presence of AC had a lower TUNEL staining. In addition, FIGS. 15C-D clearly show a breakdown of the membrane and altered morphology of oocytes cultured without AC, while oocytes cultured with AC have a normal, healthy morphology. These results clearly demonstrate that administration of recombinant AC decreases the rate of apoptosis during human oocyte maturation in vitro.

Discussion of Examples 12-15

Sphingolipid metabolism and sphingolipid-mediated signal transduction appear to be important in mammalian fertilization and early development. AC is the central enzyme in sphingolipid metabolism, hydrolyzing the pro-apoptotic lipid, ceramide, into the anti-apoptotic lipid, sphingosine-1-phosphate. Thus, AC is a rheostat helping to control a cell's fate between life and death. These Examples demonstrate that administration of recombinant AC enzyme results in a decreased rate of apoptosis in vitro in fresh or aged mouse oocytes, preventing DNA and cytoplasm fragmentation. This confirms the important role of this enzyme for oocyte survival during culture.

Example 16

Figure 16:
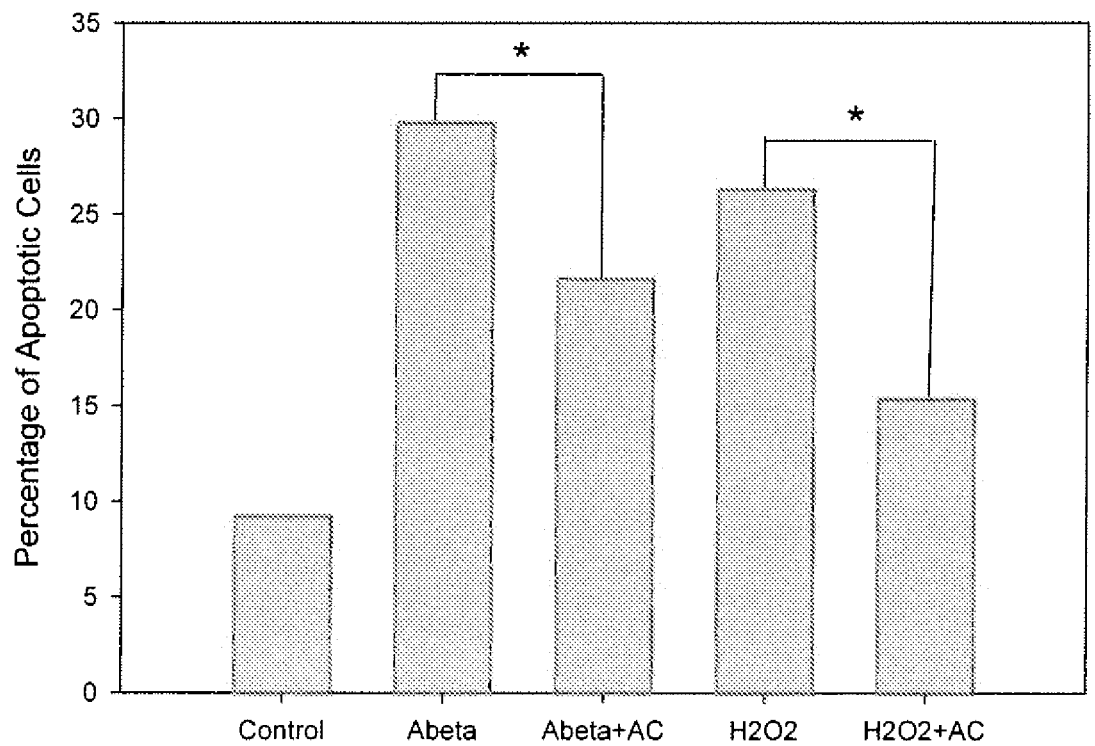
FIG. 16 is a graph of the percentage of apoptotic cells in primary rat hippocampal neuron cultures grown in normal culture media ("control"), or with amyloid-β peptide ("Abeta"), amyloid-β peptide and AC ("Abeta+AC"), hydrogen peroxide ("H2O2"), or hydrogen peroxide and AC ("H2O2+AC") added to the culture media. *p<0.01 based on three independent experiments.

Recombinant, Human Acid Ceramidase Protects Primary Rat Neurons from Stress-induced Apoptosis Primary rat hippocampal neurons were grown for 17 hours in the presence of the pathologic Alzheimer's Disease protein, amyloid-β peptide (1 mM), or under the conditions of oxidative stress (i.e., with 50 mM of hydrogen peroxide), with or without recombinant human acid ceramidase present in the culture media (2 mg/ml). Notably, when acid ceramidase was included in the culture media, apoptosis (as assessed by TUNEL staining) was significantly reduced, as shown in FIG. 16.

Example 17

Figure 17:
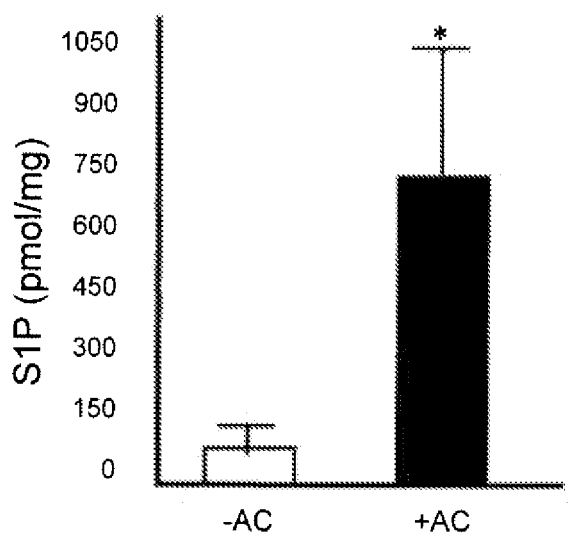
FIG. 17 is a graph of sphingosine-1-phosphate ("S1P") levels in primary rat synovial fibroblasts grown with ("+AC") or without ("−AC") human AC. *p<0.001.

Acid Ceramidase Increases the Survival and Proliferation Rate of Cat Synovial Fibroblasts Primary cat synovial fibroblasts were grown for 24 hours with or without recombinant human acid ceramidase (2 mg/ml), and the levels of the survival factor, sphingosine-1-phosphate ("S1P") were determined. As shown in FIG. 17, S1P levels was markedly higher in fibroblasts incubated with AC. This suggests that AC can be used to improve the survival rate of synovial fibroblasts in vitro.

The proliferation rate of primary cat synovial fibroblasts was determined using the MTS assay (Barltrop et al., "5-(3-Arboxymethoxyphenyl)-2-(4,5-dimenthylthiazoly)-3-(4-sulfophenyl)Tetrazolium, Inner salt (MTS) and Related Analogs of 3-(4,5-Dimethylthiazolyl)-2,5-diphenyltetrazolium Bromide (MTT) Reducing to Purple Water Soluble Formazans as Cell-viability Indicators," *Bioorg. Med. Chem. Lett.* 1:611-4 (1991), which is hereby incorporated by reference in its entirety) with or without recombinant acid ceramidase in the culture media (2 mg/ml). As shown in FIG. 18, primary synovial fibroblasts cultured in the presence of AC proliferated significantly faster than cells cultured without AC. This confirms that AC can be used to improve the survival rate of synovial fibroblasts in vitro.

Example 18

Acid Ceramidase Improves the Survival Rate of Mouse Embryonic Stem Cells

Western blot analysis was used to evaluate the total amount of AC in mouse embryonic stem cells ("ESCs"). Proteins were separated by SDS-PAGE and detected using a polyclonal antibody against the AC beta subunit. As shown in FIG. 19, the AC protein is expressed at high levels and active in ESCs. These results suggest that AC could be involved in ESC survival.

The effect of AC on the level of poly(ADP-ribose) polymerase ("PARP") and Bax, two pro-apoptotic factors, was also evaluated. ESCs were incubated for 24 hours in a humidified incubator at 37° C. in the absence or presence of AC. The cells were then lysed, and 100 mg of total protein was separated by SDS-PAGE. As shown in FIGS. 20A-C, the amount of two important pro-apoptotic factors, PARP and Bax, is reduced in the presence of AC. These results suggest that AC can potentially prolong the life-span of ESCs.

Example 19

Acid Ceramidase Protects Rat Neuronal Cell Cultures Against Apoptosis

Chemicals and Reagents

Cell culture materials were from Fisher Scientific (Pittsburgh, Pa., USA). All other biochemical reagents were from the Sigma Chemical Co. (St. Louis, Mo., USA).

Cell Culture

Neuronal progenitor cells were isolated from the adult rat hippocampus and cultured in neurobasal A medium consisting of 2% B27, 0.5 mM glutamine, 100 units/ml penicillin, 100 µg/ml streptomycin, and 10 ng/ml FGF at 37° C. in a humidified 5% $CO_2$ atmosphere (Chen et al., "Trophic Factors Counteract Elevated FGF-2-induced Inhibition of Adult Neurogenesis," *Neurobiol. Aging* 28:1148-62 (2007), which is hereby incorporated by reference in its entirety). The media was routinely changed every 2-3 days. When the cells reached ~80% confluency, they were differentiated by replacing FGF with 5 µM retinoic acid and 10% fetal calf serum. The neuronal cultures were generally used for experiments after 3-5 days of growth in the differentiation medium. At this stage, ~80% of the cells expressed the neuronal markers βIII-tubulin and microtubule-associated protein 2. Less than 5% of the cells expressed the astroglial marker GFAP or the oligodendrocyte marker O4. Thus, the differentiated cells were used as a neuronal cell culture model for subsequent experiments.

Effect of Acid Ceramidase on Ceramide Levels and Apoptosis in Neuronal Cell Cultures After 3-5 days of growth in the differentiation media, neuronal cultures were treated with 1 µM of Aβ for 30 minutes with or without 1 hour of recombinant human AC pre-treatment (1 µg/ml). Ceramide levels were verified using the DAG kinase method (He et al., "An Enzymatic Assay for Quantifying Sphingomyelin in Tissues and Plasma from Humans and Mice with Niemann-Pick Disease," *Anal Biochem.* 293: 204-11 (2001), which is hereby incorporated by reference in its entirety). Caspase 3 activity was measured using EnzCheck Caspase-3 assay kit.

Figure 21:
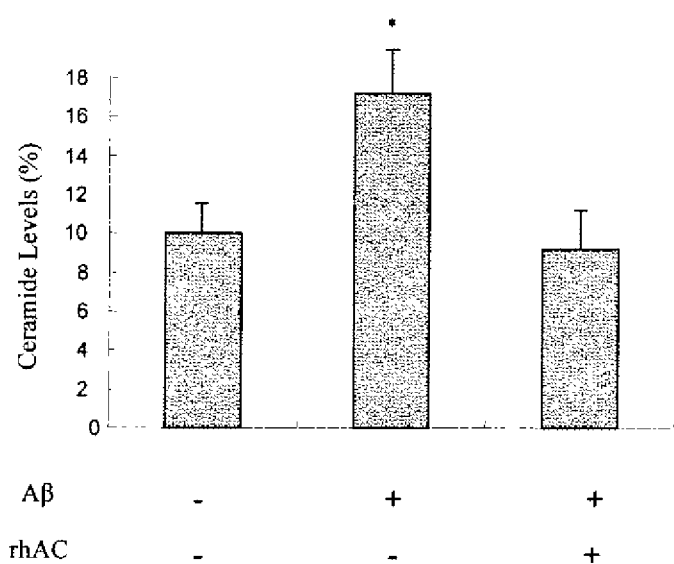
FIG. 21 is a graph of the ceramide levels in rat neuronal cell cultures with ("+") or without ("−") amyloid-β peptide ("Aβ") and/or recombinant human AC ("rhAC"). *p<0.05, compared to normal brains. Values are expressed as the mean±S.D (N=3).
Figure 22:
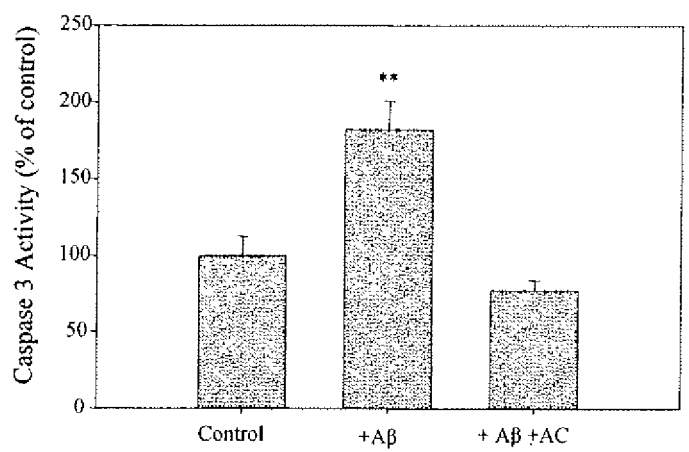
FIG. 22 is a graph of the caspase 3 activity in untreated ("control") rat neuronal cell cultures, and cultures exposed to amyloid-β peptide with ("+Aβ+AC") or without ("+Aβ") recombinant human AC pre-treatment. **p<0.01, compared to normal brains. Values are expressed as the mean±S.D. (N=3).

Acid sphingomyelinase activity is significantly elevated in the AD brain and after amyloid-β peptide treatment of neuronal cultures. As shown in FIG. 21, ceramide levels are also significantly elevated after treating neuronal cultures with Aβ. More apoptotic cells are also found as determined by caspase 3 activity, as shown in FIG. 22. Importantly, however, ceramide levels and caspase 3 activity did not increase in response to Aβ when purified, rhAC was included in the culture media, as shown in FIG. 21 and FIG. 22, suggesting that AC can be used to protect against ceramide-mediated apoptosis in neuronal cells. In summary, FIGS. 21-22 show that ceramide levels and apoptosis are reduced in the presence of AC.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of promoting the ex vivo survival of mammalian cells, said method comprising:
    providing one or more mammalian cells ex vivo, wherein the one or more mammalian cells are selected from the group consisting of eggs, primary cells, neurons, sperm, synovial fibroblasts, and embryonic stem cells; and
    treating the one or more mammalian cells with acid ceramidase under conditions effective to promote survival of the one or more mammalian cells.

2. The method of claim 1, wherein the one or more mammalian cells are provided in a culture medium and the acid ceramidase is added to the culture medium during said treating.

3. The method of claim 1, wherein the one or more mammalian cells are one or more eggs.

4. The method of claim 3, wherein the one or more eggs are unfertilized.

5. The method of claim 3, wherein the one or more eggs are fertilized.

6. The method of claim 3, wherein the one or more eggs are from a human.

7. The method of claim 1, wherein said treating is carried out with acid ceramidase in protein form.

* * * * *

SEQUENCE LISTING

```
<160> NUMBER OF SEQ ID NOS: 8

<210> SEQ ID NO 1
<211> LENGTH: 29
<212> TYPE: DNA
<213> ORGANISM: artificial
<220> FEATURE:
<223> OTHER INFORMATION: Oligonucleotide primer

<400> SEQUENCE: 1
acccaggttc catcgttgca catttcatc                                    29

<210> SEQ ID NO 2
<211> LENGTH: 31
<212> TYPE: DNA
<213> ORGANISM: artificial
<220> FEATURE:
<223> OTHER INFORMATION: Oligonucleotide primer

<400> SEQUENCE: 2
atgccacatg ggaatactgt ccaaagcaga a                                 31

<210> SEQ ID NO 3
<211> LENGTH: 30
<212> TYPE: DNA
<213> ORGANISM: artificial
<220> FEATURE:
<223> OTHER INFORMATION: Oligonucleotide primer

<400> SEQUENCE: 3
cacacaaaca catgtatgtg cacacgtgaa                                   30
```

-continued

```
<210> SEQ ID NO 4
<211> LENGTH: 24
<212> TYPE: DNA
<213> ORGANISM: artificial
<220> FEATURE:
<223> OTHER INFORMATION: Oligonucleotide primer

<400> SEQUENCE: 4
gctgccctgg aactcactca ctct                                              24

<210> SEQ ID NO 5
<211> LENGTH: 26
<212> TYPE: DNA
<213> ORGANISM: artificial
<220> FEATURE:
<223> OTHER INFORMATION: Oligonucleotide primer

<400> SEQUENCE: 5
gaggagtaga aggtggcgcg aagggg                                            26

<210> SEQ ID NO 6
<211> LENGTH: 22
<212> TYPE: DNA
<213> ORGANISM: artificial
<220> FEATURE:
<223> OTHER INFORMATION: Oligonucleotide primer

<400> SEQUENCE: 6
ggtggatgtg gaatgtgtgc ga                                                22

<210> SEQ ID NO 7
<211> LENGTH: 19
<212> TYPE: DNA
<213> ORGANISM: artificial
<220> FEATURE:
<223> OTHER INFORMATION: Oligonucleotide primer

<400> SEQUENCE: 7
ttaccgcaga acaccggcc                                                    19

<210> SEQ ID NO 8
<211> LENGTH: 22
<212> TYPE: DNA
<213> ORGANISM: artificial
<220> FEATURE:
<223> OTHER INFORMATION: Oligonucleotide primer

<400> SEQUENCE: 8
ttgacctttg gtaacatcca tc                                                22
```